(12) United States Patent
Reynaud et al.

(10) Patent No.: US 11,160,296 B2
(45) Date of Patent: Nov. 2, 2021

(54) DEACIDIFIED CRANBERRY JUICE AND PROCESS FOR PREPARING SAME

(71) Applicant: West Invest S.A.

(72) Inventors: Eric Reynaud, Luxembourg (LU);
Charles Duval, Eyguieres (FR);
Stanislas Baudouin, Perigny (FR);
Jacques Meurisse, Meylan (FR)

(73) Assignee: WEST INVEST S.A., Luxembourg (LU)

( * ) Notice: Subject to any disclaimer, the term of this patent is extended or adjusted under 35 U.S.C. 154(b) by 0 days.

(21) Appl. No.: 16/334,412

(22) PCT Filed: Sep. 19, 2017

(86) PCT No.: PCT/EP2017/073641
§ 371 (c)(1),
(2) Date: Mar. 19, 2019

(87) PCT Pub. No.: WO2018/054904
PCT Pub. Date: Mar. 29, 2018

(65) Prior Publication Data
US 2019/0216112 A1    Jul. 18, 2019

(30) Foreign Application Priority Data
Sep. 20, 2016 (FR) ..................... 16/58802

(51) Int. Cl.
*A23L 2/78* (2006.01)
*A23L 2/02* (2006.01)
(Continued)

(52) U.S. Cl.
CPC .................. *A23L 2/78* (2013.01); *A23L 2/02* (2013.01); *A23L 33/105* (2016.08); *A61K 36/45* (2013.01);
(Continued)

(58) Field of Classification Search
None
See application file for complete search history.

(56) References Cited

U.S. PATENT DOCUMENTS 4,522,836 A    6/1985 Dechow et al.
6,045,842 A    4/2000 Mozaffar et al.
(Continued)

FOREIGN PATENT DOCUMENTS

FR    2041431 A5    1/1971
WO    2010121203 A1    10/2010

OTHER PUBLICATIONS

CWP: candle Wine PRoject: Making Alcohol with cranberries; published online at least by Nov. 20, 2010 at: https://web.archive.org/web/20101120145003/https://candlewineproject.wordpress.com/2010/11/17/making-alcohol-with-cranberries/.*

(Continued)

*Primary Examiner* — Patricia A George
(74) *Attorney, Agent, or Firm* — Buchanan Ingersoll & Rooney P.C.

(57) ABSTRACT

The invention relates to a deacidified juice, as well as a process for deacidifying a cranberry juice to be deacidified that is eluted on a bed or a weak anion exchange resin at a rate (BV/h) such that the deacidified cranberry juice leaving the elution has a pH=$pKa_1$ (malic acid)<pH<pKa (benzoic acid).

The invention also relates to a food composition that comprises this deacidified fruit juice.

19 Claims, 9 Drawing Sheets

(51) Int. Cl.
*A61K 36/45* (2006.01)
*A23L 33/105* (2016.01)

(52) U.S. Cl.
CPC ....... *A23V 2002/00* (2013.01); *A23V 2200/30* (2013.01); *A23V 2250/21166* (2013.01); *A23V 2300/34* (2013.01); *A61K 2236/00* (2013.01)

(56) References Cited

U.S. PATENT DOCUMENTS

| | | | |
|---|---|---|---|
| 2004/0197448 | A1 | 10/2004 | Chung et al. |
| 2005/0175760 | A1 | 8/2005 | Chung et al. |
| 2010/0009049 | A1 | 1/2010 | Smith |
| 2013/0266706 | A1* | 10/2013 | Bussmann ................ A23L 2/80 426/490 |

OTHER PUBLICATIONS

Rozoy: Deacidification of Cranberry Juice by Electrodialysis with Bipolar Membranes; J. Agric. Food Chern. 2015, 63, 642-651 ; © 2014 American Chemical Society.*

Dardel: All ion exchange resins; updated online on Oct. 5, 2020 at: http://dardel.info/IX/AllResins.php?sort=5&filtre=1 (Year: 2020).*

Rozoy: Deacidification of Cranberry Juice by Electrodialysis with Bipolar Membranes; DOI: 10.1021/jf502824f J. Agric. Food Chem. 2015, 63, 642-651. (Year: 2015).*

Sondhi: Crossflow Filtration (Ceramic and Hollow Fiber Membranes) in the Citrus Industry; ASME 2008 Citrus Engineering Conference CEC2008 Mar. 20, 2008, Lake Alfred, Florida, USA CEC2008-5403. (Year: 2008).*

Raz: Cranberry Juice and Urinary Tract Infection; Clinical Infectious Diseases, vol. 38, Issue 10, May 15, 2004, pp. 1413-1419. (Year: 2004).*

CI: Cook's Info: Malic Acid: published online at least by Dec. 5, 2015 at: https://web.archive.org/web/20151205093919/https://www.cooksinfo.com/malic-acid (Year: 2015).*

Dupont: AMBERLITE™ FPA55 Ion Exchange Resin Food-grade, Gel, Acrylic, Weak Base Anion Exchange Resin; Form No. 45-D00759-en, Rev. Sep. 2, 2019. (Year: 2019).*

Bazinet Laurent et al., "Evolution of cranberry juice physic-chemical paramenters during phenolic antioxidant enrichment by electrodialysis with filtration membrane", Separation and Purification Technology, vol. 87, Nov. 23, 2011, pp. 31-39.

International Search Report (PCT/ISA/210) dated Dec. 7, 2017, by the European Patent Office as the International Searching Authority for International Application No. PCT/EP2017/073641.

Serre Elodiet et al., "Deacidification of cranberry juice by electrodialysis: Impact of membrane types and configurations on acid migration and juice physucichemical characteristics", Separation and Purification Technology, vol. 163, Feb. 26, 16, pp. 228-237.

Vera E. et al., "Comparison between different ion exchange resins for the deacidification of passion fruit juice", Journal of Food Engineering, 2003, pp. 199-207.

Vera E. et al., "Comparison of Different methods for deacidification of clarified passion fruit juice", Journal of Food Engineering, vol. 59, 2003, pp. 361-367.

* cited by examiner

DEACIDIFIED CRANBERRY JUICE AND PROCESS FOR PREPARING SAME

TECHNICAL FIELD OF THE INVENTION

The invention relates to a deacidified cranberry juice, a process for deacidifying the juice, and various uses of the deacidified juice obtained using the process.

The cranberry is a close relative of the North American blueberry, the European whortleberry and various other berries from the genus *Vaccinium*. All of these plants share that they are small and procumbent, grow in acidic soils and yield berries that are particularly rich in antioxidants.

The cranberry is a fruit measuring 10 to 20 mm in diameter, with a bright red color when mature. Its flavor is very characteristic, since it has a high acidity and astringency.

The cranberry is well known for its health benefits and the prevention of certain diseases.

The health benefits of cranberries are in particular explained by the fact that this plant contains various types of flavonoids, which participate in preventing the occurrence of diseases such as cardiovascular disease, certain cancers and various illnesses related to aging.

The main flavonoids of the cranberry are:
- anthocyans (also called "anthocyanosides" or "anthocyanins"), which impart the characteristic red color of the fruit;
- anthocyanidins;
- flavonols, and in particular:
  - flavan-3-ol monomers (for example, catechin, epicatechin, gallocatechin, and epigallocatechin);
  - flavan-3-ol polymers (for example, proanthocyanidins (also called "condensed tannins"));
- gallotannins and ellagitannins (also called "hydrolysable tannins");
- flavonols such as quercetin, in glycosylated and/or aglycone form).

"Anthocyans" refer to anthocyanidin heterosides, i.e., anthocyanidins carrying sugars. The osidic part of the anthocyans can be a monosaccharide (glucose, galactose, rhamnose), a disaccharide (rutinose made up of a glucose connected to a rhamnose, xyloglucose) or a trisaccharide. Most anthocyanosides are anthocyanidin 3-monosides and 3,5-diosides.

"Anthocyanidins" refer to a sub-class of flavonoids, the basic structure of which is made up of two aromatic rings A and B joined by 3 carbons forming, with oxygen, the C cycle. The six most common anthocyanidins are: cyanidin, delphinidin, pelargonidin, peonidin, petunidin and malvidin.

In the cranberry, sugars represent about 45 to 67% by weight of sugars relative to the total weight of the dry extract. The sugars present in particular include glucose, fructose, sucrose and sorbitol.

Lastly, the main organic acids present in the cranberries are quinic acid, citric acid, malic acid and phenolic acids such as hydroxybenzoics and hydroxycinnamics. The cranberry contains, per 100 g: about 0.05 g of hydroxybenzoic acids (primarily represented by benzoic acid) and less than 0.1 g of hydroxycinnamic acids, represented primarily by p-coumaric, sinapinic and caffeic acids.

The traditional use of the cranberry is essentially based on transformed forms of its fruit, namely:
- the jellied fruit,
- juice, most often concentrated or dried, and
- extracts obtained by purification through various processes of different compounds contained by this plant (including proanthocyanidins), or from the fruit, the juice, or the skins and pulps, referred to jointly as marc, derived from the juice production activity.

The cranberry has a very low natural pH, close to 2.3 when the fruit is fully matured. This highly acidic nature makes the use of natural cranberry juice very delicate in food compositions. Indeed, many people refuse to drink it, due to its excessively acidic and astringent taste.

This is why cranberry juice is generally not consumed pure or as a majority component of an agri-food formulation of the juice type. Indeed, in the fruit juice formulations based on cranberry juice that are currently marketed, the weight content of cranberry juice is comprised between no more than 15% and 20% relative to the total mass of the juice. It is generally about 7%.

SUMMARY OF THE INVENTION

One aspect of the invention relates to a process for deacidifying a cranberry juice to be deacidified.

One aspect of the invention relates to a deacidified cranberry juice.

One additional aspect of the invention targets a deacidified cranberry juice capable of being obtained using the process according to the invention.

One additional aspect of the invention targets a food composition that comprises deacidified cranberry juice, for example using the process described below.

DETAILED DESCRIPTION OF THE INVENTION

The invention relates to a deacidified cranberry juice, characterized in that:
- the pH of the deacidified juice is comprised between 3 and 5, more preferably between 3.2 and 3.8;
- the quinic acid/malic acid ratio of the deacidified juice is greater than 0.7, preferably greater than 0.8, alternatively from about 0.8 to about 1 or from about 0.85 to about 0.99;
- the deacidified juice does not contain added sugars, masking agents, such as a base or chelating agent, or buffer.

One embodiment consists of a process for deacidifying a cranberry juice to be deacidified, characterized in that:
- the cranberry juice to be deacidified is eluted on a weak anion exchange resin to provide a deacidified cranberry juice after elution;
- the weak anion exchange resin is a resin of the acrylic or styrene type;
- the cranberry juice to be deacidified is eluted on said resin at a rate (BV/h) such that the deacidified cranberry juice after elution has a pH=$pKa_1$ (malic acid) <pH<pKa (benzoic acid);

where "$pKa_1$ (malic acid)" represents the pKa of the $1^{st}$ acidity of the malic acid, and "pKa (benzoic acid)" represents the pKa of the benzoic acid.

Furthermore, it should be noted that a pH value greater than about 6 causes a substantial modification (or in other words, an alteration), generally irreversible, of the structure of the flavonoids.

In the case of the cranberry, among these compounds of interest that are particularly sensitive to an excessively high pH value, examples include anthocyans, the structural change of which will be visible due to the fact that the coloring of the cranberry juice (with a red natural shade) will first lean toward bluish shades if the pH is around 6, then toward green shades if the pH is between 8 and 9, and lastly black if the pH is comprised between 9 and 10.

In other words, if the pH of the cranberry juice reaches a threshold value of about 6, this causes a chemical breakdown of certain compounds of interest naturally contained by this juice. Once the compound of interest has been altered, it may no longer have its natural properties, which are for example antioxidant properties and which contribute to giving the cranberry juice beneficial health effects (in particular preventive effects regarding certain diseases outlined above). This is why it is crucial to avoid any chemical stress on the compounds of interest, in particular the flavonoids, during a process for deacidification of the cranberry juice, in order to prevent them from being altered and then losing their beneficial health properties.

One preferred embodiment is therefore a process in which the pH of the deacidified juice does not exceed (preferably at any time during the process) the threshold pH value, or a pH of about 6.

The inventors of the present invention have developed a new process for deacidifying cranberry juice, which is completely effective, since it does not alter the compounds of interest as described above. Furthermore, the process according to the invention may be implemented in juice production and transformation installations, without requiring modifications of the existing devices.

The process according to the invention also has the advantages of providing a cranberry juice with:
  a pH standardized at the desired value for the desired application, this value being defined as the setpoint to be achieved;
  a color similar to that of the natural fruit juice and therefore familiar to its consumers;
  in the case of cranberry juice, a concentration index that may be comprised between 5 and 65 degrees Brix depending on whether a subsequent concentration step will be carried out on the deacidified cranberry juice;
  in the case of cranberry juice, a much less astringent taste relative to that of the natural cranberry juice, which makes it very appropriate in food and medical applications, without requiring the addition of sugars and/or chemical masking compounds, or diluting it;
  organoleptic properties extremely similar to those of the natural fruit juice and therefore perfectly recognizable by its consumers.

As a result, the deacidified cranberry juice according to the invention can be used in fruit juice formulations at weight content levels higher than those currently implemented, which are at most 15 to 20%, generally 7%. This has the advantage of providing fruit juice formulations based on cranberry juice that contain higher content levels of the various compounds of interest contained by this juice, such as vitamins and flavonoids (i.e., antioxidants) that were outlined above, relative to the cranberry juice-based fruit juices that are currently commercially available.

According to one embodiment, the deacidification process is carried out in a column containing the anion exchange resin, said column having a column inlet and a column outlet, and said elution consists of circulating said cranberry juice to be deacidified at least once, so as to obtain the deacidified juice after elution.

One embodiment of the process consists of:
  adjusting the circulation flow rate of said juice to be deacidified in the column at a rate equal to or greater than 10 BV/hour, for example between 10 BV/hour and 250 BV/hour,
  using a volume of cranberry juice ranging from 1 to 20, and preferably from 5 to 10 Bv;
  using a column such that the ratio of the height of the column to the diameter of the column is comprised between 0.3 and 1, more preferably between 0.4 and 0.6; or about 0.5;
such that
  the pH of the juice at the outlet of the column does not exceed the pH threshold value from which the at least one compound of interest is altered, and preferably $pKa_1$ (malic acid)<pH<pKa (benzoic acid).

In one embodiment, the deacidification process is carried out in a deacidification device that comprises at least:
  a container configured to contain the cranberry juice to be deacidified, which comprises at least one compound of interest,
  a container for receiving the deacidified juice, and
  a column containing an anion exchange resin, said column having a column inlet and a column outlet,
wherein said process comprises at least one step that consists of circulating said juice to be deacidified at least once in said column so as to obtain a deacidified juice, said process being characterized in that said circulation rate of said juice in the column is comprised between 10 BV/hour and 250 BV/hour and is adjusted such that:
  the pH of the juice leaving the column does not exceed a threshold pH value beyond which the at least one compound of interest is altered,
  the pH of the juice in the container receiving the deacidified juice increases to a predetermined pH value.

"BV" is the acronym for "bed volume", i.e., the volume of resin in the column. Indeed, in the technical field of juice deacidification, implemented in columns filled with ion exchange resin, it is perfectly normal to express the circulation (or in other words, passage) flow rate of the juice in the column in BV/hour. This has the advantage of indicating the flow rate in a normalized manner, i.e., irrespective of the volume of the column. This is why, in the following description, the circulation flow rate of the cranberry juice will in particular be expressed in BV/hour.

Thus, during the deacidification process according to the invention, the circulation flow rate of the cranberry juice in the column containing an anion exchange resin can vary while remaining comprised between 10 BV/hour and 250 BV/hour.

In one embodiment of the process, the volume (BV) of cranberry juice is from 1 to 20, preferably from 5 to 10.

One element contributing to the originality of the process according to the invention lies in the fact that the cranberry juice circulates at least once in a column containing an anion exchange resin at a high flow rate that is at least 10 BV/hour and that it is also adjusted such that the pH of the juice leaving the column does not exceed a pH threshold value from which compounds of interest naturally contained by the cranberry juice can be altered.

This has the advantage that the cranberry juice will be deacidified owing to the anion exchange resin without said compounds of interest experiencing chemical stresses, such that the deacidified cranberry juice retains all of its compounds of interest (for example, the flavonoids such as anthocyans) that have health benefits.

The total proanthocyanidin content of the deacidified cranberry juice according to the present invention is substantially the same as the cranberry juice to be deacidified having led to said deacidified cranberry juice.

The content in proanthocyanidins, phenolic acids and flavonoids of the deacidified cranberry juice is substantially the same as the cranberry juice to be deacidified having led to said deacidified cranberry juice.

The content in inorganic cations of the deacidified cranberry juice is substantially the same as the cranberry juice to be deacidified having led to said deacidified cranberry juice. The inorganic cations are in particular potassium, calcium and sodium (K, Ca and Na).

Preferably, the treated juice has a content in proanthocyanidins, phenolic acids, flavonoids or organic cations that is not substantially lower than the content of the cranberry juice to be deacidified. Still more preferably, the treated juice has a content of two, three or four of said proanthocyanidins, phenolic acids, flavonoids and organic cations that is not substantially lower than the content of the cranberry juice to be deacidified.

"Substantially" refers to a content not varying beyond measurement errors, preferably not varying outside the range of 95-105%, or 98-102%, and more preferably 99-101% of the content.

The deacidified juice according to the present invention does not contain added sugars, masking agent, such as a base or a chelating agent, or buffer.

The invention refers to deacidified cranberry juice according to the invention, concentrated or not, for example having a concentration index that may be comprised between 5 and 65 degrees Brix, and for example around 50 Brix.

The process according to the invention does not require "preconditioning", for example partial deactivation of the reactivity of the anion exchange resin using an acid (e.g., in solution), such as a food organic acid like citric acid, malic acid, ascorbic acid or a combination of the latter.

In one embodiment of the invention, the deacidification device comprises a plurality of columns, for example preferably between 2 and 10, still more preferably between 3 and 6. In one embodiment of the invention, the deacidification device comprises three columns.

The implementation of a plurality of columns in juice treatment processes is completely typical and known by those skilled in the art. Thus, this embodiment of the deacidification process according to the invention is within the reach of one skilled in the art.

The fact that the deacidification device includes several columns makes it possible to increase the performance of the deacidification process according to the invention.

In one embodiment of the process according to the invention, said cranberry juice to be deacidified is circulated in a loop between said container configured to contain the fruit juice to be deacidified and the column. In this embodiment of the invention, the container configured to contain the juice to be deacidified and the container for receiving the deacidified juice are a same and single container. Thus, the juice to be deacidified circulates in a loop such that it goes from the container to the inlet of the column, traverses the column, then from the outlet of the column, rejoins the container.

In one embodiment of the process according to the invention, said cranberry juice to be deacidified is circulated partially in a loop, such that after leaving the column:
- a first part of the deacidified cranberry juice rejoins the container configured to contain the juice to be deacidified, and
- a second part of the deacidified cranberry juice joins the container for receiving deacidified cranberry juice.

The implementation of partial circulation in a loop in fruit juice treatment processes is completely typical and known by those skilled in the art. The partial circulation in a loop is in particular used when one wishes to concentrate the deacidified juice. Thus, this embodiment of the deacidification process according to the invention is within the reach of one skilled in the art.

In another embodiment of the process according to the invention, the cranberry juice to be deacidified is circulated just once in said column.

These embodiments of the process according to the invention as described above, namely implementing a plurality of columns, as well as circulation by a single passage in the column or circulation in a loop, if applicable circulation in a partial loop, can be combined, thus providing other embodiments that can be considered in the context of the present invention.

The at least one compound of interest can be one of the flavonoids naturally present in the cranberry juice that were discussed above. It may be chosen from among anthocyans, anthocyanidins, flavanols, gallotannins, ellagitannins and flavonols. Preferably, the compound of interest is an anthocyan.

The alteration of the compound of interest has been explained above. It involves a structural modification of the compound of interest that is generally irreversible. Once the compound of interest has been altered, it may no longer have its beneficial health properties, for example its antioxidant properties.

In one embodiment of the invention, the process according to the invention comprises a step for pretreatment of the cranberry juice to be deacidified.

This pretreatment step may consist of clarifying the juice using any existing technique fully within the reach of one skilled in the art. Examples of these clarification techniques include centrifugation and filtration (in particular membrane, diatom or plate filtration).

For example, the clarification is advantageously done until obtaining a cranberry juice having a turbidity below 500 NTU (Nephelometric Turbidity Unit), preferably below 100, still more preferably below 25 NTU.

This pretreatment step has the advantage of preventing clogging of the column.

During the process according to the invention, an anion exchange resin is used to capture acids in order to deacidify the cranberry juice. More specifically, an exchange occurs in the column of an anion on an adsorbent (namely the resin, which is a polymer) against another anion.

Preferably, the resin is a weak anion exchange resin. For example, the weak anion exchange resins are ternary amines that are neutral at a pH greater than 10 and ionized at a pH lower than 10. Consequently, it is understood that a weak exchange resin refers to a resin whose cation function is dissociated based on the pH of the solution.

Weak anion exchange resins have the advantage of being very specific to weak acids and multivalent acids. Yet as explained above, the cranberry juice to be deacidified comprises organic acids, which are weak acids. Indeed, the pKa (i.e., the acidity constant) of the $1^{st}$ acidity of the malic acid is 3.4, that of the quinic acid is 4.3 and that of the benzoic acid is 4.2.

In the context of the present invention, "weak acid" refers to an acid that is not completely dissociated in water. An acid is weaker when its pKa is higher.

In another embodiment, an acid is captured and a hydroxylated ion is released; this allows the pH to increase and a water molecule to form.

The exchange equilibrium equation (I) is as follows:

$$\text{Resin-NH+Acid-H+H}_2\text{O} \Longrightarrow \text{Resin-NH}^+_2\text{-Acid+OH}^- \quad \text{(I)}$$

Preferably, the anion exchange resin is an exchange resin of the acrylic or styrene type. Advantageously, it is an anion exchange resin of the acrylic type. The acrylic-type anion exchange resin preferably has a capacity between 1.6-3.2. The resin also has an initial exchange speed equal to or greater than +0.10 unit of pH/minute observed after 5 minutes of contact of the juice to be deacidified with the resin in a volume ratio of 5:1 (juice:resin). The particle size of the resin varies between 300 and 600 µM.

One example of a weak anion exchange resin of the acrylic type is the CR5550 model marketed by the company DOW CHEMICAL under the trade name AMBERLITE®.

Advantageously, the ratio of the height of the column to the diameter of the column is comprised between 0.3 and 1, more preferably between 0.4 and 0.6. Particularly preferably, this ratio is 0.5.

When said ratio is comprised between 0.3 and 1, this has the advantage of being able to cause the cranberry juice to be deacidified to circulate in the column at very high flow rates exceeding those typically used during deacidification processes for juice in columns filled with anion exchange resin, at pressures comprised between 2 bars and 5 bars.

The total volume of the column may represent between 1 and 2, preferably between 1.3 and 1.7, still more preferably between 1.4 and 1.6 times the volume of the resin that it contains.

Preferably, the circulation of the cranberry juice to be deacidified is done in an up flow column. In the field of ion exchange resins, it is quite traditional to implement circulation of the juice to be treated in the up flow mode, when the resin captures chemical species (in the case at hand, weak acids). Indeed, when the resin captures species, it increases in volume and the fact that the circulation of the juice is in the up flow mode prevents pressure increase phenomena that could block this expansion of the resin.

The height of the bed of the anion exchange resin can be comprised between 30 cm and 200 cm, preferably between 50 cm and 100 cm.

In one embodiment of the process, the pH of the cranberry juice leaving the column never exceeds the threshold pH value increased by 0.5 pH unit.

Preferably, in the case of cranberry juice, the threshold pH value from which the at least one compound of interest is altered is comprised between 6 and 9.

In embodiments of the process according to the invention, the pH of the cranberry juice leaving the column is higher than the pKa of at least a predetermined weak acid naturally contained by the cranberry juice. These embodiments allow a more selective capture of at least one determined weak acid from among the weak acids naturally contained by the cranberry juice. If the pH of the cranberry juice circulating in the column is below the pKa of a determined weak acid naturally contained by this juice, then this acid is captured very little by the anion exchange resin.

The selective capture of at least one weak acid during the deacidification process according to the invention is particularly advantageous. Indeed, it is necessary to deacidify the cranberry juice to make it consumable without dilutions and/or additions of other compounds, but certain acids that it contains also have beneficial health and/or flavor properties for the juice. This is why it is interesting not to capture these acids.

In the cranberry juice, malic acid is highly concentrated and gives this juice an overly acidic and astringent taste. This is why an effort is made to capture it with the anion exchange resin during the process according to the invention, in order to reduce its concentration thereof. However, the quinic and benzoic acids also present in the natural cranberry juice have the advantage of being natural preservatives. It is useful to keep the majority of them in the cranberry juice and therefore to prevent them from being captured by the anion exchange resin during the process according to the invention.

In light of the pKa values of the malic, quinic and benzoic acids recalled above, if one wishes to selectively capture the malic acid during the deacidification process according to the invention, the pH value of the cranberry juice leaving the column must be higher than the pKa of the malic acid, but lower than the pKa of the quinic and benzoic acids.

In one embodiment of the invention, the pH value of the cranberry juice leaving the column is comprised between the pKa of the $1^{st}$ acidity of the malic acid (i.e., around 3.4) and the pKa of the benzoic acid (i.e., around 4.2). In this embodiment, little of the benzoic and quinic acids is captured by the anion exchange resin. Their concentration is therefore kept practically constant in the cranberry juice, despite the deacidification of said juice during the process according to the invention.

Thus, a pH value of the cranberry juice leaving the column of about 3.5 is particularly appropriate to more selectively capture the malic acid during the deacidification process according to the invention, and therefore to maintain quinic and benzoic acid concentrations in the deacidified juice that are substantially equal to those of the cranberry juice before deacidification thereof.

In one embodiment, the cranberry juice leaving the column has a quinic acid/malic acid ratio greater than 0.7, preferably from 0.8 to 1 or from 0.85 to 0.99.

Of course, in these embodiments of the invention in which one or several weak acids are further selectively captured, the deacidified cranberry juice retains its organoleptic properties and therapeutic benefits, since the pH value of the cranberry juice leaving the column is also below the threshold pH value from which compounds of interest such as flavonoids can be altered.

Preferably, in the case of cranberry juice, the determined pH value is comprised between 3 and 5, more preferably between 3.2 and 3.8.

Quite preferably, in the case of cranberry juice, the determined pH value is about 3.5. In other words, in this embodiment of the process according to the invention, the cranberry juice is circulated in the column until the pH of the cranberry juice that was initially comprised between 2.3 and 2.5 (i.e., before deacidification thereof) reaches the value of about 3.5 at the end of the deacidification process.

The circulation of the cranberry juice in the column can be done using a pump equipping the deacidification device. Preferably, the pump is a volume displacement pump.

The deacidification device may further comprise a pH meter to measure the pH of the deacidified cranberry juice leaving the column.

In one embodiment of the invention, the circulation flow rate of the cranberry juice in the column is adjusted using a PID (Proportional, Integral, Derivative) regulator equipping the deacidification device. A PID regulator is a device traditionally used in the industry that makes it possible to perform closed-loop slaving of a process.

Thus, in one embodiment of the invention, the deacidification device further comprises a pump and a pH meter to measure the pH of the deacidified juice leaving the column and, from the pH values of the cranberry juice leaving the column, which are measured by said pH meter and received by the PID regulator, said PID regulator, from a calculation algorithm, delivers a flow rate command signal to the pump such that the circulation flow rate of said cranberry juice in the column is comprised between 10 BV/hour and 250 BV/hour and is adjusted such that:
- the pH of the cranberry juice leaving the column does not exceed a threshold pH value from which the at least one compound of interest is altered,
- the pH of the cranberry juice in the container for receiving the deacidified cranberry juice increases to a determined pH value.

In one embodiment of the invention, the device further comprises a pH meter for measuring the pH in the container containing the deacidified cranberry juice. Thus, it is possible to monitor the evolution of the pH of the deacidified juice, and in particular to monitor whether it has reached the determined pH value.

In the embodiments of the invention in which the resin selectively captures at least one determined weak acid, the circulation flow rate of the cranberry juice is further adjusted such that the pH of the cranberry juice leaving the column is greater than the pKa of said at least one determined weak acid.

The adjustment of the PID regulator, i.e., in particular the development of the calculation algorithm for delivering a flow rate command signal to the pump, is fully within the reach of one skilled in the art. Indeed, one skilled in the art will know, from routine tests, how to adjust the PID regulator to adjust the circulation flow rate in the column of the cranberry juice, during the process according to the invention.

The exchange speed in the anion exchange resin depends on the diffusion speed of the anions inside the resin (the degree of cross-linking being one of the factors of this diffusion speed) and the diffusion speed at the resin-cranberry juice interface (diffusion through the liquid film around each grain of resin). In general, the exchange speed increases with the fineness of the resin particles, the mobility of the exchanged anions, the concentration and the temperature of the considered juice. By increasing the circulation speed of the cranberry juice through the resin bed, the resin-cranberry juice contact time is limited. The exchange is therefore limited, which makes it possible to adjust the pH at the outlet of the column.

If the cranberry juice circulation flow rate is above the exchange equilibrium speed of equation (I) outlined above, then the exchange reaction is incomplete, and the resin does not have time to capture all of the acids present in the cranberry juice.

The more the circulation flow rate increases, the more the pH of the outlet of the column will tend to decrease. On the contrary, the more the circulation flow rate decreases, the more the pH of the cranberry juice at the outlet of the column will tend to increase.

Thus, by regulating the circulation flow rate of the cranberry juice in the column, it is possible to adjust the pH leaving the column.

At the beginning of the process according to the invention, the anion exchange resin includes many active sites capable of capturing the acids, which leads to a significant variation in the pH of the cranberry juice between the inlet and the outlet of the column. In order to avoid an excessively high pH of the cranberry juice leaving the column (i.e., above the threshold pH value from which the compounds of interest are altered), it is necessary for the circulation flow rate of the cranberry juice in the column to be high at the beginning of the process such that all of the acids of the cranberry juice do not have time to be captured by the active sites of the resin.

For example, in the case of cranberry juice, the kinetics as applied make it possible to preferably attach the malic acid, and thus captures a portion of the malic acid with a high selectivity.

Next, as the active sites of the resin are saturated, the circulation flow rate of the cranberry juice in the column can be decreased. Thus, the adjustment of the circulation flow rate of the cranberry juice in the column during the process is essential in the context of the present invention.

For example, at the beginning of the process according to the invention, i.e., during about the first 2 to 4 minutes of the circulation of the cranberry juice in the column, the flow rate is preferably comprised between 100 BV/hour and 150 BV/hour. This circulation flow rate is much higher than the circulation flow rates traditionally implemented in an ion exchange column for the deacidification of juice, which are generally about 5 BV/hour.

In order for the pH of the juice leaving the column not to exceed the threshold value from which the compounds of interest such as the flavonoids are altered, and if applicable for it to be greater than the pKa of at least one determined weak acid naturally contained by the cranberry juice, it is necessary to impose a circulation flow rate of the juice that is very high, of more than 100 BV/hour at the very beginning of the process. Next, this circulation flow rate may be decreased and kept constant such that the pH of the deacidified cranberry juice increases gradually to the determined pH value, which, in the case of cranberry, is preferably about 3.5.

At the end of at least one passage in the column by the juice to be deacidified, the deacidification process according to the invention may further comprise a step for concentrating the deacidified cranberry juice. For example, it may involve a technique such as reverse osmosis or evaporation.

This additional step for concentration of the deacidified cranberry juice is fully within the reach of one skilled in the art.

Furthermore, in order to recover the acids that have been captured by the anion exchange resin during the passage of the cranberry juice, it is possible to perform, at the end of the deacidification process according to the invention, a step for saturation of the resin. Indeed, the acids captured by the resin may be of interest in applications other than juice. For example, in the case of cranberry juice, this regeneration will make it possible to leverage the malic acid thus captured during the process according to the invention.

The saturation step is perfectly within the reach of one skilled in the art. For example, it may be carried out with a hydrochloric acid solution, preferably at a concentration of 1 mol/L (73 g/L of resin).

Furthermore, a step for regeneration of the anion exchange resin can be carried out in order to be able to perform, with this same resin, another deacidification of a cranberry juice.

This anion exchange resin regeneration step is also fully within the reach of one skilled in the art. For example, it may be done with a sodium hydroxide solution at 1 mol/L (80 g/L of resin).

At the end of the deacidification process for a cranberry juice, it is thus possible to proceed as follows:
- a step for saturation of the resin is carried out, for example as described above;
- optionally followed by rinsing with water, preferably a quick rinse;
- then a regeneration step, for example as described above;
- optionally followed by one or several rinses with water (for example a slow rinse, then a fast rinse).

The present invention also relates to a food composition that comprises cranberry juice, for example deacidified according to the inventive process, as described above.

In food compositions, the cranberry juice, concentrated or not (for example having a concentration index that may be comprised between 5 and 65 degrees Brix, and for example about 50 Brix), has the advantage of being able to replace products developed with exogenous sugar additions such as sucrose or any other simple or complex sugars that are harmful to health.

The food composition may be a carbonated or noncarbonated beverage. For example, it may be a fruit juice.

Aside from beverages, the food composition may also be chosen from among sorbets, ice creams, dairy products and sauces.

Examples of food compositions according to the invention are:
- iced teas, in particular iced teas comprising a mixture of cranberry with raspberry, lime or mango;
- carbonated beverages comprising a mixture of cranberry with lemon, grapefruit or guarana;
- nonalcoholic concentrated syrups comprising a mixture of cranberry with pink grapefruit, blood orange, vineyard peach or grenadine;
- syrups for coffees and infusions with a cranberry base;
- alcoholic beverages, for example liqueurs (in particular liqueurs with an alcohol content of 25);
- cocktails with a base of cranberry and mojito or vodka;
- dairy products;
- vinaigrettes, for example vinaigrettes with a base of cranberry and raspberry or balsamic vinegar;
- savory sauces, for example savory sauces comprising a mixture of cranberry and pepper, pesto, fried onion, shallot or lime;
- sauces of the barbecue type with a base of cranberry and optionally hot peppers;
- dessert toppings, for example dessert toppings comprising a mixture of cranberry with red fruits, stracciatella, chocolate, cane sugar, coconut or honey.

Thus, the food composition may be chosen from among beverages, sorbets, ice creams, sauces, dessert toppings and vinaigrettes.

The present invention also relates to a nutraceutical composition that comprises deacidified cranberry juice according to the invention as described above.

The present invention also relates to a composition that comprises deacidified cranberry juice as described above for use thereof in the prevention of urinary infections.

The invention will be better understood using the detailed description provided below in reference to the appended drawing, as a non-limiting example, of embodiments of deacidification devices in which the process according to the invention can be carried out, as well as experimental data relative to said process.

DESCRIPTION OF THE FIGURES

FIG. 1 schematically shows a device in which the deacidification process according to the invention can be carried out according to a first embodiment in which the cranberry juice to be deacidified circulates a single time in the anion exchange column.

FIG. 2a schematically shows a device 10 in which the deacidification process according to the invention can be carried out according to a second embodiment in which the cranberry juice to be deacidified circulates in a loop in the anion exchange column.

FIG. 2b schematically shows a device 100 in which the deacidification process according to the invention can be carried out according to a third embodiment in which the cranberry juice to be deacidified circulates in a loop partially in an anion exchange column.

FIG. 2c schematically shows a device 1000 equipped with three anion exchange columns and in which the deacidification process according to the invention can be carried out according to a fourth embodiment in which the cranberry juice to be deacidified circulates in a closed loop in the three anion exchange columns.

Figure 1:
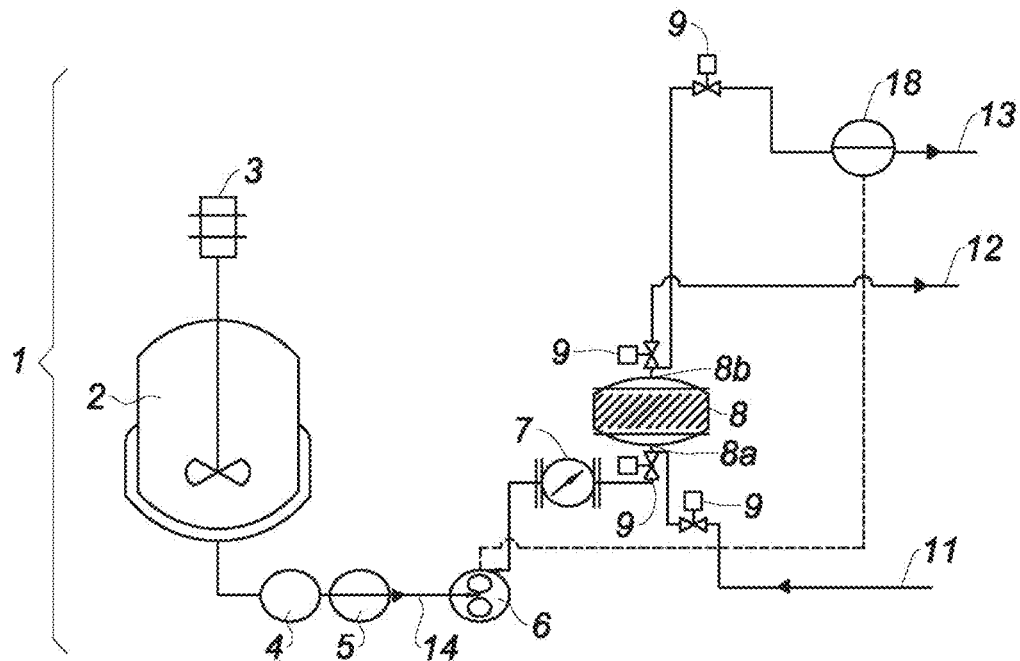
FIG. 1 schematically shows a device in which the deacidification process according to the invention can be carried out according to a first embodiment.

The structural elements shared by the devices 1, 10, 100 and 1000 and that have the same function bear the same numerical reference irrespective of FIGS. 1, 2a, 2b and 2c.

The devices 1, 10, 100 and 1000 comprise:
a container 2 configured to contain the cranberry juice to be deacidified, in other words, a supply container for containing the raw juice to be deacidified;
a motor 3 for agitating the contents of the container 2;
an anion exchange column 8 (the device 1000 comprises three columns 8), having a column inlet 8a and a column outlet 8b;
a regulating flowmeter 4 for the juice;
a temperature probe 5;
a pump 6;
a pressure indicator 7;
valves 9;
a pH meter 18 for measuring the pH of the juice leaving the column 8b;
an intake channel 11 for a regenerating solution of the column 8;
a discharge channel 12 for discharging the regeneration solution after it passes in the column 8;
an intake channel 4 for the juice to be deacidified in the column 8.

The regeneration solution is used during a step for regenerating the anion exchange resin contained by the column 8. This regeneration step was mentioned above.

The flowmeter 4, the temperature probe 5 and the pump 6 are therefore arranged on the channel 14.

The dotted lines in FIGS. 1, 2a, 2b and 2c schematically show a PID regulator. From pH values at the outlet of the column 8b that are measured by the pH meter 18 and received by the PID regulator, said PID regulator, from a calculation algorithm, delivers a flow rate command signal to the pump 6 such that the circulation flow rate of said juice in the column 8 is comprised between 10 BV/hour and 250 BV/hour and is adjusted as outlined above.

The devices 1, 10 and 1000 further comprise a discharge channel 13 for discharging the deacidified juice from the column 8.

In the case of the device 1, said channel 13 is connected to a deacidified juice receiving container not shown in FIG. 1 so as to collect the juice having circulated in the column 8 and which has therefore been deacidified.

In the case of the device 10, the juice to be deacidified circulates in a loop between the container 2 and the column 8 when the deacidification process according to the invention is carried out. The container 2 is therefore also the receiving container for the deacidified juice. The channel 13 is connected to the container 2 such that the juice having circulated in the column 8 is reintegrated into the container 2.

The same is true for the device 1000, which comprises three columns 8. The channel 13 is connected to the container 2 such that the juice having circulated in the three columns 8 is reincorporated into the container 2.

The device 100 is configured so that the juice circulates in a loop partially between the container 2 and the column 8.

Figure 2A:
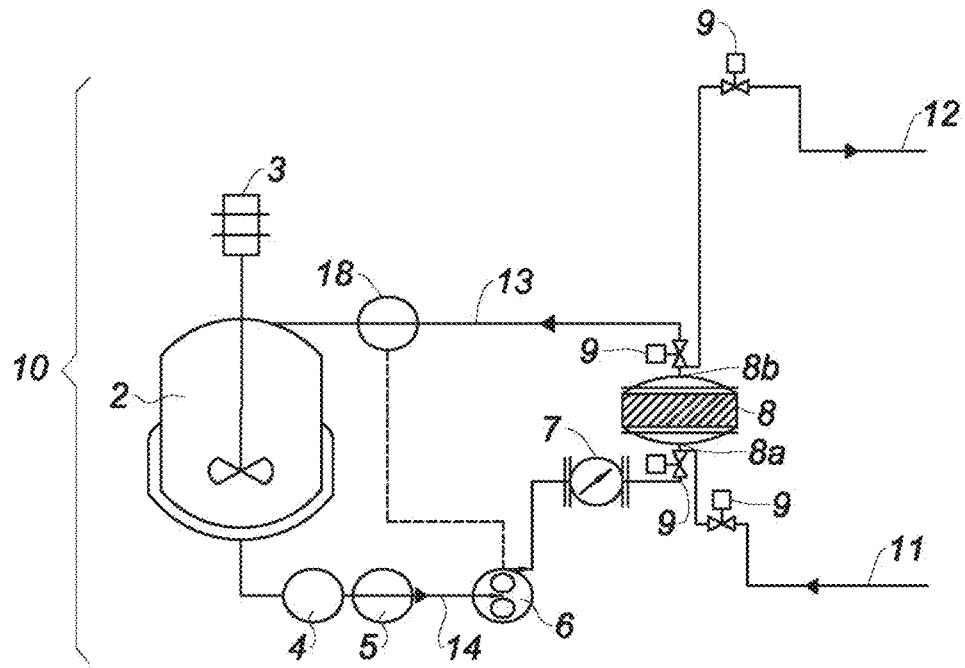
FIG. 2a schematically shows a device in which the deacidification process according to the invention can be carried out according to a second embodiment.
Figure 2B:
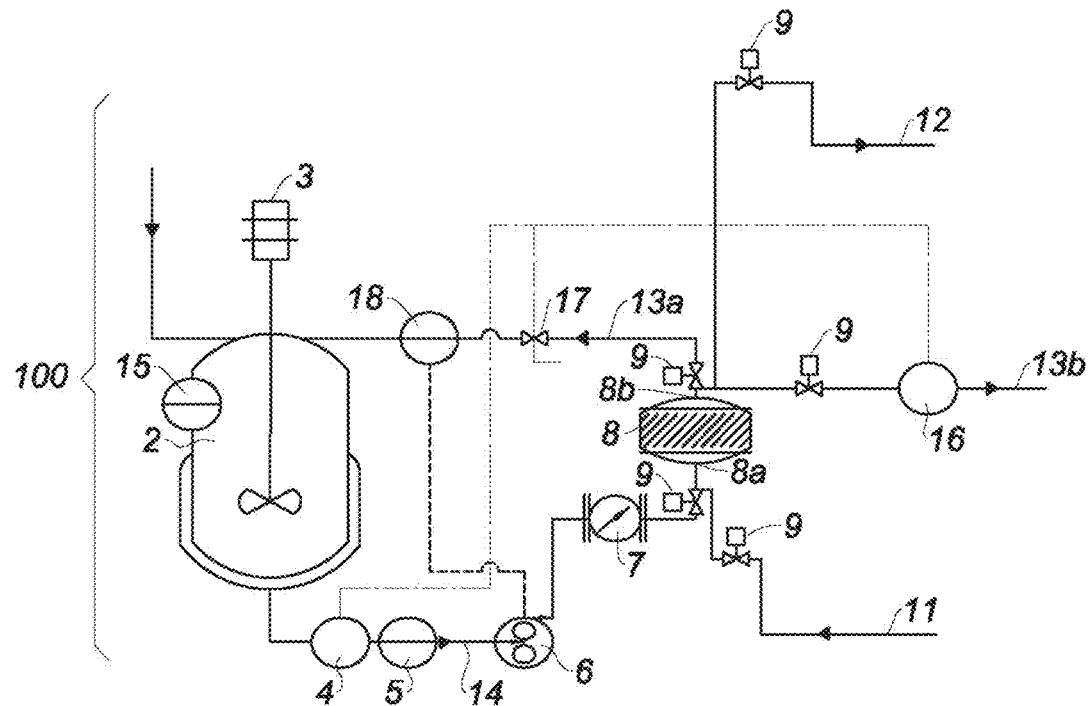
FIG. 2b schematically shows a device in which the deacidification process can be carried out according to a third embodiment.
Figure 2C:
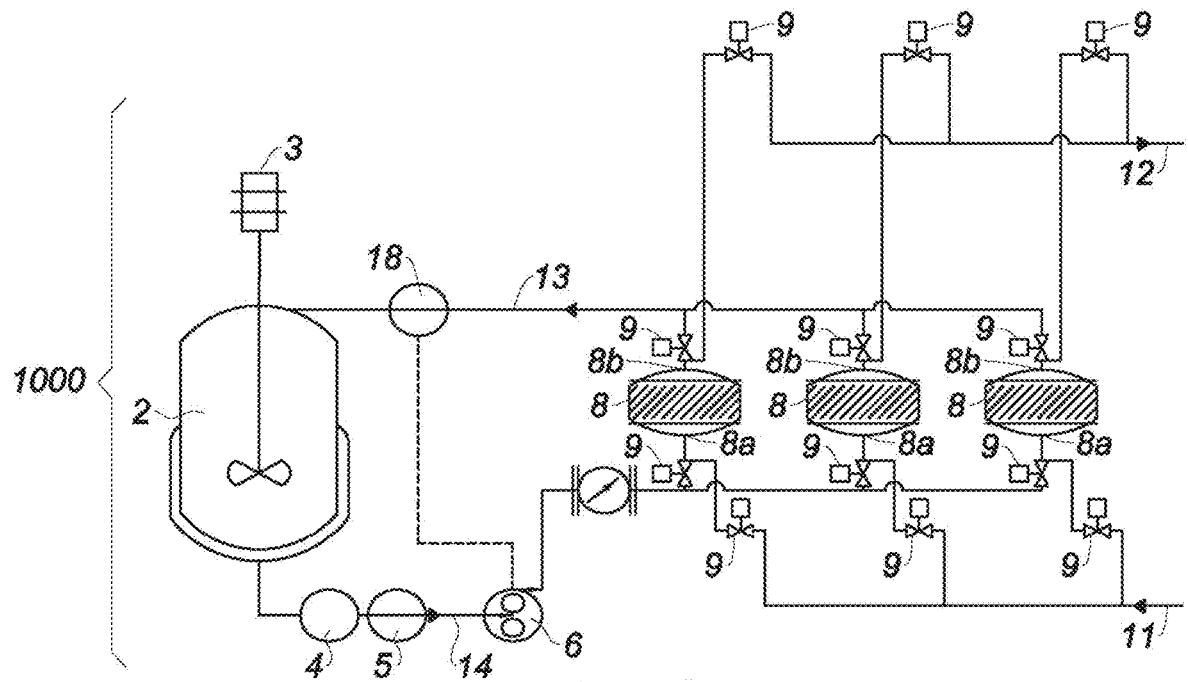
FIG. 2c schematically shows a device in which the deacidification process can be carried out according to a fourth embodiment.

The device 100 further comprises a level measuring means 15, a flowmeter 16, an optional rate valve 17, a first discharge channel 13a for discharging a first part of the deacidified juice from the column 8 toward the container 2, and a second discharge channel 13b for discharging a second part of the deacidified juice from the column 8 toward a container for receiving this second part of the juice that is not shown in FIG. 2b.

The adjustment of the optional rate valve 17 allows the desired distribution of the deacidified juice between its reincorporation into the container 2 and its discharge toward a container for receiving the deacidified juice. As explained above, the second part of the deacidified juice, which is therefore discharged by the channel 13b, may be subject to a concentration treatment fully within the reach of one skilled in the art.

In FIG. 2b, the dotted lines connecting the optional rate valve 17 to the flowmeter 4 and the flowmeter 16 schematically show the regulating loop of the PID regulator making it possible to adjust the opening of the optional rate valve 17 to control the recycling flow rate (i.e., the flow rate of deacidified cranberry juice that is reincorporated into the container 2) based on the differential between the cranberry juice flow rate at the inlet of the column 8a and the collection flow rate of the deacidified juice measured by the flowmeter 16.

EXPERIMENTAL PART

The experiments that are outlined below relate to the implementation of the deacidification of a cranberry juice that initially had the following characteristics:
a concentration index of 7.6 degrees Brix;
a pH of 2.47;
a red color;
a total acidity of 0.098 equivalent/L;
a malic acid concentration of 9.47 g/L;
a quinic acid concentration of 6.63 g/L.

The dry matter of the cranberry juice was estimated by measuring the Brix index with a sucrose scale.

The assay of the acids was done by high-performance liquid chromatography (HPLC) with:
a column marketed by the company BIO-RAD under the commercial name Aminex HPX-87H measuring 7.8× 300;
an eluent that was a solution of sulfuric acid at 3 mmol/L implemented with an elution flow rate of 1 mL/minute at 60° C.;
the analysis of the cations is done by ICP (Inductively Coupled Plasma), on an Agilent-brand device.

The experiments can be broken down in the following three parts:
a) deacidification of the cranberry juice in the stationary mode (or in other words, in "Batch" mode) in a beaker containing an anion exchange resin;
b) the deacidification of the cranberry juice by single passage in a column filled with an anion exchange resin;
c) the deacidification of the cranberry juice by circulation in a loop in the column filled with an anion exchange resin.
All of the experiments outlined below were done at 20° C.
During all of these deacidification experiments, the determined pH value of the cranberry juice to be reached was set at 3.5. In other words, 3.5 was the "target value" to be reached for the pH of the cranberry juice at the end of all of these deacidification experiments.

The 5 anion exchange resins that were used during these experiments had the features outlined in table 1 below, namely:
- the model,
- the company marketing the resin and under what commercial name,
- the structure,
- the total theoretical capacity indicated by its supplier and expressed in equivalent/L,
- the particle size of the beads of resin (expressed in μm),
- the uniformity coefficient (hereinafter abbreviated "UC"), where UC=d60/d10 (diameter for 60% of the mass of the beads/diameter for 10% of the mass of the beads).

TABLE 1 outlining the characteristics of the 5 resins used during the experiments

|  | Resin 1 | Resin 2 | Resin 3 | Resin 4 | Resin 5 |
|---|---|---|---|---|---|
| Model | S5221 | CR5550 | A365 | Dowex66 | FPA51 |
| Company | LANXESS | DOW CHEMICAL | RHOM & HAAS | DOW CHEMICAL | DOW CHEMICAL |
| Commercial name | LEWATIT ® | AMBERLITE ® | DUOLITE ® | AMBERLITE ® | AMBERLITE ® |
| Structure | acrylic gel | acrylic gel | acrylic gel | Macro-cross-linked polystyrene | Macro-cross-linked polystyrene |
| Capacity (equivalent/L) | 3.0-3.2 | 1.6 | 3.5 | 1.3 | 1.3 |
| Size (μm) | 550 | 450 | 550 | 550 | 550 |
| UC | 1.8 | 1.2 | 1.8 | 1.1 | 1.8 |

A—Deacidification of the Cranberry Juice in Stationary Mode

Two tests (E1 and E2) were carried out for each of resins 1 to 5 according to the following experimental protocol:

In a beaker, 50 mL of cranberry juice was placed in contact with 10 mL of the selected resin so as to obtain a mixture.

The mixture was agitated continuously with a magnetized agitator and the pH of the supernatant was measured regularly.

Once equilibrium was reached, the initial exchange speed was determined from the variation of the pH observed after 5 minutes.

Table 2 below outlines, as a function of time (expressed in minutes), the pH measured in the mixture containing resin 1 during the $1^{st}$ test (E1) and the $2^{nd}$ test (E2), as well as the mean value of the calculated pH (mean pH).

TABLE 2 outlining the pH values measured in the mixture containing resin 1

|  | Time (minutes) | | | | | | | |
|---|---|---|---|---|---|---|---|---|
|  | 0 | 0.5 | 1 | 2 | 3 | 5 | 10 | 20 |
| pH E1 | 2.53 | 2.69 | 2.77 | 2.90 | 2.99 | 3.16 | 3.49 | 4.09 |
| pH E2 | 2.53 | 2.65 | 2.74 | 2.86 | 2.96 | 3.12 | 3.45 | 4.00 |
| Mean pH | 2.53 | 2.67 | 2.76 | 2.88 | 2.98 | 3.14 | 3.47 | 4.05 |

For resin 1, an initial exchange speed of 0.12 pH unit/minute was determined.

Table 3 below outlines, as a function of time (expressed in minutes), the pH measured in the mixture containing resin 2 during the $1^{st}$ test (E1) and the $2^{nd}$ test (E2), as well as the mean value of the calculated pH (mean pH).

TABLE 3 outlining the pH values measured in the mixture containing resin 2

|  | Time (minutes) | | | | | | | |
|---|---|---|---|---|---|---|---|---|
|  | 0 | 0.5 | 1 | 2 | 3 | 5 | 10 | 20 |
| pH E1 | 2.53 | 2.87 | 2.99 | 3.17 | 3.32 | 3.53 | 3.94 | 4.02 |
| pH E2 | 2.53 | 2.83 | 2.96 | 3.11 | 3.24 | 3.46 | 3.76 | 3.88 |
| Mean pH | 2.53 | 2.85 | 2.98 | 3.14 | 3.28 | 3.50 | 3.80 | 3.95 |

For resin 2, an initial exchange rate of 0.19 pH unit/minute was determined.

Table 4 below outlines, as a function of time (expressed in minutes), the pH measured in the mixture containing resin 3 during the $1^{st}$ test (E1) and the $2^{nd}$ test (E2), as well as the mean value of the calculated pH (mean pH).

TABLE 4 outlining the pH values measured in the mixture containing resin 3

|  | Time (minutes) | | | | | | | |
|---|---|---|---|---|---|---|---|---|
|  | 0 | 0.5 | 1 | 2 | 3 | 5 | 10 | 20 |
| pH E1 | 2.53 | 2.64 | 2.71 | 2.75 | 2.81 | 2.9 | 3.16 | 3.53 |
| pH E2 | 2.53 | 2.65 | 2.69 | 2.74 | 2.79 | 2.84 | 3.09 | 3.48 |
| Mean pH | 2.53 | 2.65 | 2.70 | 2.75 | 2.80 | 2.87 | 3.13 | 3.51 |

For resin 3, an initial exchange speed of 0.07 pH unit/minute was determined.

Table 5 below outlines, as a function of time (expressed in minutes), the pH measured in the mixture containing resin 4 during the $1^{st}$ test (E1) and $2^{nd}$ test (E2), as well as the mean value of the calculated pH (mean pH).

TABLE 5 outlining the pH values measured in the mixture containing resin 4

|  | Time (minutes) | | | | | | | |
|---|---|---|---|---|---|---|---|---|
|  | 0 | 0.5 | 1 | 2 | 3 | 5 | 10 | 20 |
| pH E1 | 2.53 | 2.64 | 2.66 | 2.72 | 2.76 | 2.84 | 3.00 | 3.22 |
| pH E2 | 2.53 | 2.64 | 2.66 | 2.71 | 2.76 | 2.84 | 2.99 | 3.22 |
| Mean pH | 2.53 | 2.64 | 2.66 | 2.72 | 2.76 | 2.84 | 3.00 | 3.22 |

For resin 4, an initial exchange speed of 0.06 pH unit/minute was determined.

Table 6 below outlines, as a function of time (expressed in minutes), the pH measured in the mixture containing resin 5 during the $1^{st}$ test (E1) and $2^{nd}$ test (E2), as well as the mean value of the calculated pH (mean pH).

TABLE 6 outlining the pH values measured in the mixture containing resin 5

| | Time (minutes) | | | | | | | |
|---|---|---|---|---|---|---|---|---|
| | 0 | 0.5 | 1 | 2 | 3 | 5 | 10 | 20 |
| pH E1 | 2.53 | 2.75 | 2.83 | 2.95 | 3.03 | 3.16 | 3.38 | 3.62 |
| pH E2 | 2.53 | 2.79 | 2.86 | 2.95 | 3.03 | 3.16 | 3.37 | 3.58 |
| Mean pH | 2.53 | 2.77 | 2.85 | 2.95 | 3.03 | 3.16 | 3.38 | 3.60 |

For resin 5, an initial exchange speed of 0.13 pH unit/minute was determined.

In light of these tables 2 to 6 and the initial exchange speeds for resins 1 to 5, one can see that:
- the tests done with resin 4 do not make it possible to achieve the target pH value of 3.5: at the end of the tests, the pH is stagnant at the value of 3.22;
- only the tests done with resins 1 and 2 greatly exceed this target pH value of 3.5;
- the tests done with resins 3 and 5 just barely reach this target pH value of 3.5 (respectively with values of 3.51 and 3.6);
- resins 1 and 2 have the same initial exchange speed and make it possible to achieve the highest pH at the end of deacidification in a beaker.

The experiments in sections B) and C) that follow were done only with resins 1 and 2.

Experiments B) and C) perform the deacidification of the cranberry juice with a column filled with an anion exchange resin (resins 1 or 2).

The circulation flow rate of the cranberry juice in the column is expressed below in mL/minute, but also in BV/hour.

For all of the experiments in sections B and C, the resin volume was 50 mL, with the exception of the $4^{th}$ and $5^{th}$ experiments with resin 1 in section C), for which the resin volume was 460 mL.

B—Comparative Examples: Deacidification of Cranberry Juice by Single Passage in an Anion Exchange Column (Resins 1 and 2) with a Circulation Flow Rate of 5 Bv/Hour These experiments done with an anion exchange column without recirculation made it possible to determine the exchange capacity of resins 1 and 2 on the cranberry juice as described above.

The experimental protocol was as follows:
Resins 1 and 2 were each loaded in a column. The cranberry juice was percolated through the resin bed so as to be deacidified.

FIG. 1 schematically shows the device 1 in which these experiments of section B were done.

The circulation flow rate of the cranberry juice in the column is always 5 BV/hour (4 mL/minute) for these experiments done with resin 1 and resin 2.

The circulation flow rate being constant at 5 BV/hour, said deacidification experiments of the cranberry juice of this section B are comparative experiments relative to the deacidification process according to the invention.

Table 7 below outlines, for the experiment done with resin 1, based on the volume (expressed in L) of cranberry juice passed through the column:
- the By;
- the concentration index expressed in degrees Brix;
- pHB: the pH values of the deacidified cranberry juice measured at the outlet of column 8a by the pH meter 18;
- pHA: the pH values of the deacidified cranberry juice that were measured in the receiving container of said juice (not shown in FIG. 1).

TABLE 7 outlining the BV values, concentration index in degrees Brix, pHA and pHB for the experiment done with resin 1

| Volume (L) | BV | °Bx | pHB | pHA |
|---|---|---|---|---|
| Cranberry juice to be deacidified | | 7.6 | | 2.47 |
| 50 | 1 | 1.4 | 9.41 | 9.41 |
| 100 | 2 | 4.3 | 9.31 | 9.32 |
| 150 | 3 | 4.6 | 9.21 | 9.21 |
| 200 | 4 | 4.8 | 9.11 | 9.11 |
| 250 | 5 | 4.9 | 9.01 | 9.02 |
| 300 | 6 | 5.2 | 8.67 | 8.87 |
| 350 | 7 | 5.3 | 4.53 | 7.72 |
| 400 | 8 | 5.7 | 3.62 | 4.58 |
| 450 | 9 | 6.1 | 3.29 | 3.99 |
| 500 | 10 | 6.2 | 3.14 | 3.74 |
| 550 | 11 | 6.7 | 3.00 | 3.55 |
| 600 | 12 | 6.9 | 2.91 | 3.41 |
| 650 | 13 | 7 | 2.84 | 3.32 |
| 700 | 14 | 7.1 | 2.80 | 3.21 |
| 750 | 15 | 7.1 | 2.76 | 3.16 |
| 800 | 16 | 7.2 | 2.73 | 3.11 |
| 850 | 17 | 7.3 | 2.70 | 3.08 |
| 900 | 18 | 7.3 | 2.67 | 3.01 |

Figure 3:
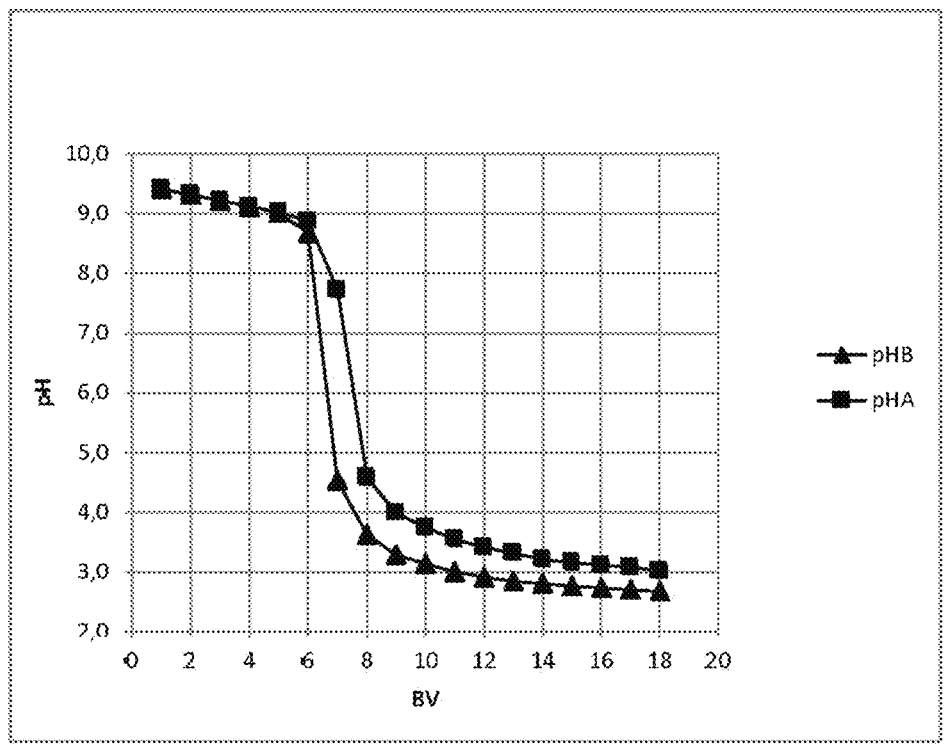
FIG. 3 is a graph of the evolution of the pH values as a function of the BV over the course of deacidification experiments by single passage of cranberry juice in an ion exchange column filled with a first resin at a flow rate of 5 BV/hour.

FIG. 3 is a graph showing the evolution of the pHA and pHB values as a function of the BV.

In light of table 7 in FIG. 3, one can see a constant decrease in the pHA and pHB values.

The pHA values are always greater than or equal to those of the pHB. This can be explained logically because:
- pHA represents a "mean" pH of the cranberry juice, since it is measured in the container receiving, throughout the entire experiment, the cranberry juice after its single passage through the column, and
- pHB represents an "instantaneous" pH of the cranberry juice that is measured just after leaving the column.

The pHA and pHB values are greater than 9 for 5 BV, or for about the $1^{st}$ hour of experimentation.

During the experiment, the color of the cranberry juice leaving the column was black, then became green, blue, and lastly, red. The quantity of fixed color appears high.

The cranberry juice in the container for receiving the deacidified cranberry juice reached the target value of 3.5 after 11 BV (pHA at 11 BV: 3.55 and pHA at 12 BV: 3.41).

For this cranberry juice collected in the container for receiving deacidified cranberry juice, the drop in pH is observed between 7 and 8 BV (pHA at 6 BV: 8.87 and pHA at 7 BV: 7.72).

During this experiment, the cranberry juice was therefore subjected to a significant variation in pH, which led to the modification of the color and precipitation (in other words, the alteration) of compounds of interest such as anthocyans.

Table 8 below outlines:
the concentrations of malic and quinic acids present in the cranberry juice:
  raw (i.e., the cranberry juice to be deacidified);
  deacidified in the receiving container when 12 BV of raw cranberry juice has passed through column 2 filled with resin 1;
  deacidified in the receiving container when 18 BV of raw cranberry juice has passed through column 2 filled with resin 1;
the ratio of the quinic acid concentration to the malic acid concentration.

TABLE 8 outlining the concentrations of malic and quinic acid present in the raw cranberry juice, at 12 BV and 18 BV

| Cranberry juice | g/L | | quinic acid/malic acid ratio |
|---|---|---|---|
| | malic acid | quinic acid | |
| raw | 9.47 | 6.63 | 0.70 |
| Deacidified (12 BV) | 4.89 | 4.46 | 0.91 |
| Deacidified (18 BV) | 6.74 | 6.07 | 0.90 |

In light of table 8, one can see that during this deacidification experiment with resin 1:
  the quinic and malic acids are captured by resin 1: their concentration respectively goes from 6.63 to 4.46 and from 9.47 to 4.89 when the cranberry juice is deacidified up to 12 BV, i.e., just after having reached the target value of 3.5;
  the malic acid is more fixed by resin 1 than the quinic acid. The ratio goes from 0.7 to 0.9. The quinic acid therefore has a lower affinity with resin 1.

Table 9 below outlines, for the experiment done with resin 2, based on the volume (expressed in L) of cranberry juice having passed through the column:
  the Bv;
  the concentration index expressed in degrees Brix;
  pHB as defined above;
  pHA as defined above.

TABLE 9 outlining the BV values, concentration index in degrees Brix, pHA and pHB for the experiment done with resin 2

| Volume (L) | BV | °Bx | pHB | pHA |
|---|---|---|---|---|
| Cranberry juice to be deacidified | | 7.6 | | 2.47 |
| 50 | 1 | 1.2 | 9.84 | 9.84 |
| 100 | 2 | 4.9 | 9.95 | 9.88 |
| 150 | 3 | 5.1 | 9.82 | 9.78 |
| 200 | 4 | 5.1 | 9.86 | 9.85 |
| 250 | 5 | 5.1 | 9.74 | 9.73 |
| 300 | 6 | 5.1 | 9.47 | 9.62 |
| 350 | 7 | 5.4 | 3.85 | 5.31 |
| 400 | 8 | 6.3 | 3.20 | 4.08 |
| 450 | 9 | 6.9 | 2.97 | 3.67 |
| 500 | 10 | 7.3 | 2.85 | 3.46 |
| 550 | 11 | 7.3 | 2.77 | 3.32 |
| 600 | 12 | 7.2 | 2.75 | 3.21 |
| 650 | 13 | 7.2 | 2.72 | 3.11 |
| 700 | 14 | 7.2 | 2.69 | 3.05 |
| 750 | 15 | 7.3 | 2.64 | 3.02 |

Figure 4:
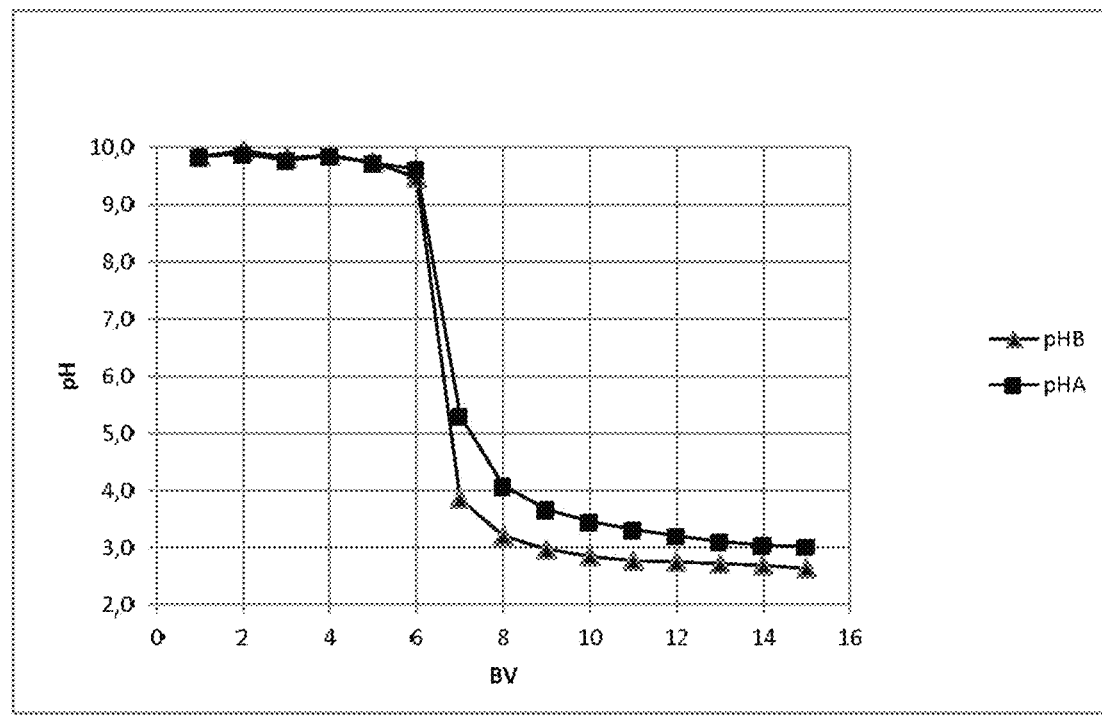
FIG. 4 is a graph of the evolution of the pH values as a function of the BV during deacidification experiments by a single passage of cranberry juice in an anion exchange column filled with a second resin at a flow rate of 5 BV/hour.

FIG. 4 is a graph showing the evolution of the pHA and pHB values as a function of the BV.

In light of table 9 in FIG. 4, one can see a constant decrease in the pHA and pHB values.

The pHA and pHB values are greater than 9 for 6 BV, or during more than the 1$^{st}$ hour of the experiment.

During the experiment, the color of the cranberry juice leaving the column was black, then became green, blue, and lastly, red. The quantity of fixed color appears high.

The cranberry juice in the receiving container reached the target value of 3.5 after 10 BV (pHA at 9 BV: 3.67 and pHA at 10 BV: 3.46).

For this cranberry juice collected in the receiving container, the drop in pH is observed between 6 and 7 BV (pHA at 6 BV: 9.62 and pHA at 7 BV: 5.31).

During this experiment, the cranberry juice has therefore undergone a significant pH variation, which has caused the modification in the color and precipitation (in other words, the alteration) of compounds of interest such as anthocyans.

Table 10 below outlines:
the concentrations of malic and quinic acids present in the cranberry juice:
  raw (i.e., the cranberry juice to be deacidified);
  deacidified in the receiving container when 10 BV of raw cranberry juice has passed through the column filled with resin 2;
  deacidified in the receiving container when 15 BV of raw cranberry juice has passed through the column filled with resin 2;
the ratio of the quinic acid concentration to the malic acid concentration.

TABLE 10 outlining the concentrations of malic and quinic acid present in the raw cranberry juice, at 10 BV and 15 BV

| Cranberry juice | g/L | | ratio quinic acid/malic acid |
|---|---|---|---|
| | malic acid | quinic acid | |
| raw | 9.47 | 6.63 | 0.70 |
| Deacidified (10 BV) | 5.11 | 5.91 | 1.16 |
| Deacidified (15 BV) | 8.29 | 6.90 | 0.83 |

In light of table 10, one can see that during this deacidification experiment with resin 2:
  the quinic and malic acids are captured by resin 2: their concentration respectively goes from 6.63 to 5.91 and from 9.47 to 5.11 when the cranberry juice is deacidified up to 10 BV, i.e., just after having reached the target value of 3.5;
  the malic acid is more fixed by resin 2 than the quinic acid. The ratio goes from 0.7 to 0.83. The quinic acid therefore has a lower affinity with resin 2.

By comparing tables 8 and 10, one can see that:
resin 2 captures much less quinic acid than resin 1;
resin 2 has a slightly lower exchange capacity than resin 1. Indeed, it captures the malic and quinic acids less than resin 1.

C—Deacidification of Cranberry Juice by Circulation in a Loop in an Anion Exchange Column The experiments in this section C were carried out in an anion exchange column with loop circulation. Resins 1 and 2 were each loaded into a column.

At the outlet of the column, the cranberry juice effluent was reintroduced into the supply tub.

FIG. 2a schematically shows the device 10 in which these experiments were done with circulation of the cranberry juice to be deacidified in a loop.

With a column filled with resin 1, five experiments were done in order to verify the load of cranberry juice to be deacidified (i.e., the volume of cranberry juice to be deacidified circulated in a loop).

The measured pH of the deacidified cranberry juice measured at the outlet of column 8b by the pH meter 18 is hereinafter called "pH2".

The measured pH of the cranberry juice measured in container 2 by a pH meter not shown in FIG. 2a is hereinafter called "pH1".

The $1^{st}$ experiment was done with a cranberry juice load of 8 BV.

For this $1^{st}$ experiment, table 11 below outlines, as a function of time (expressed in minutes):
- the pH1 and pH2 values;
- the flow rate of cranberry juice circulating in the column (expressed in mL/minutes and in BV/hour). The flow rate is always comprised between 10 BV/hour and 250 BV/hour.

TABLE 11 outlining the values of pH 2, pH 1 and the circulation flow rate of cranberry juice with a load of 8 BV

| Time (minutes) | pH2 | pH1 | Flow rate (mL/minute) | Flow rate (BV/hour) |
|---|---|---|---|---|
| 1 | 5.01 | 2.56 | 90 | 108.0 |
| 2 | 4.09 | 2.57 | 90 | 108.0 |
| 4 | 3.2 | 2.72 | 63 | 75.6 |
| 5 | 3.29 | 2.78 | 45 | 54.0 |
| 7 | 3.61 | 2.8 | 27 | 32.4 |
| 8 | 3.6 | 2.86 | 27 | 32.4 |
| 9 | 3.58 | 2.88 | 18 | 21.6 |
| 10 | 3.58 | 2.88 | 18 | 21.6 |
| 11 | 3.65 | 2.89 | 18 | 21.6 |
| 12 | 3.77 | 2.91 | 18 | 21.6 |
| 13 | 3.82 | 2.93 | 18 | 2.16 |
| 15 | 3.84 | 2.96 | 18 | 21.6 |
| 17 | 3.86 | 3.00 | 18 | 21.6 |
| 19 | 3.84 | 3.04 | 22.5 | 27.0 |
| 21 | 3.72 | 3.08 | 27 | 32.4 |
| 23 | 3.69 | 3.16 | 27 | 32.4 |
| 25 | 3.69 | 3.16 | 27 | 32.4 |
| 27 | 3.7 | 3.2 | 27 | 32.4 |
| 30 | 3.72 | 3.25 | 27 | 32.4 |
| 35 | 3.75 | 3.32 | 27 | 32.4 |
| 36 | 3.75 | 3.36 | 36 | 43.2 |
| 40 | 3.74 | 3.39 | 45 | 54.0 |
| 44 | 3.77 | 3.46 | 45 | 54.0 |
| 47 | 3.79 | 3.5 | 54 | 64.8 |

Figure 5:
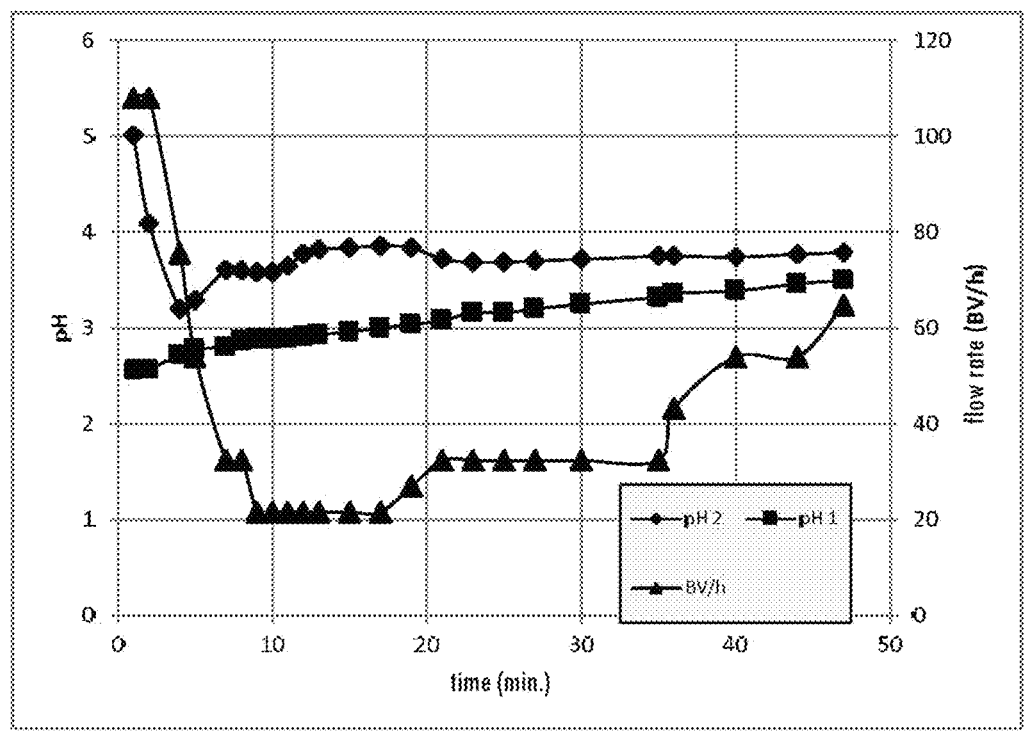
FIG. 5 is a graph showing the evolution of the pH values, and the circulation flow rate as a function of time for deacidification experiments carried out with the first resin and with recirculation at a load of 8 BV.

FIG. 5 is a graph showing the evolution of pH1, pH2 and the flow rate expressed in BV/hour as a function of time for this $1^{st}$ experiment with circulation in a loop with a cranberry juice load of 8 BV.

In light of table 11 and FIG. 5, one can in particular see that:
- the pH of the cranberry juice in the container reached the target value of 3.5 after 47 minutes of loop circulation; this $1^{st}$ experiment thus corresponds to a first implementation of the deacidification process according to the invention;
- at times 1 minute, then 2 minutes, the pH of the cranberry juice at the column outlet was respectively 5.01, then 4.09; next, after 4 minutes, it was 3.2.

the cranberry juice at the outlet of the column still had a pH less than or substantially equal to 5. The process according to the invention is therefore not likely to alter the compounds of interest, such as anthocyans.

The $2^{nd}$ experiment was done with a cranberry juice load of 10 BV.

For this $2^{nd}$ experiment, table 12 below outlines, as a function of time (expressed in minutes):
- the pH1 and pH2 values;
- the flow rate of cranberry juice circulating in the column (expressed in mL/minutes and in BV/hour). The flow rate is always comprised between 10 BV/hour and 250 BV/hour.

TABLE 12 outlining the values of pH2, pH1 and the circulation flow rate of cranberry juice with a load of 10 BV

| Time (minutes) | pH2 | pH1 | Flow rate (mL/minute) | Flow rate (BV/hour) |
|---|---|---|---|---|
| 1 | 3.78 | 2.48 | 100 | 120 |
| 2 | 3.21 | 2.53 | 80 | 96 |
| 3 | 3.24 | 2.56 | 60 | 72 |
| 4 | 3.26 | 2.59 | 50 | 60 |
| 6 | 3.35 | 2.63 | 40 | 48 |
| 8 | 3.44 | 2.67 | 30 | 36 |
| 10 | 3.45 | 2.70 | 30 | 36 |
| 12 | 3.5 | 2.72 | 20 | 24 |
| 15 | 3.62 | 2.76 | 20 | 24 |
| 20 | 3.59 | 2.82 | 20 | 24 |
| 25 | 3.57 | 2.87 | 20 | 24 |
| 30 | 3.55 | 2.92 | 20 | 24 |
| 35 | 3.67 | 2.95 | 10 | 12 |
| 40 | 3.75 | 2.98 | 10 | 12 |
| 50 | 3.75 | 3.05 | 10 | 12 |
| 60 | 3.73 | 3.10 | 10 | 12 |
| 80 | 3.68 | 3.19 | 10 | 12 |
| 120 | 3.63 | 3.31 | 10 | 12 |
| 150 | 3.61 | 3.35 | 10 | 12 |
| 180 | 3.6 | 3.37 | 10 | 12 |
| 240 | 3.59 | 3.39 | 10 | 12 |

Figure 6:
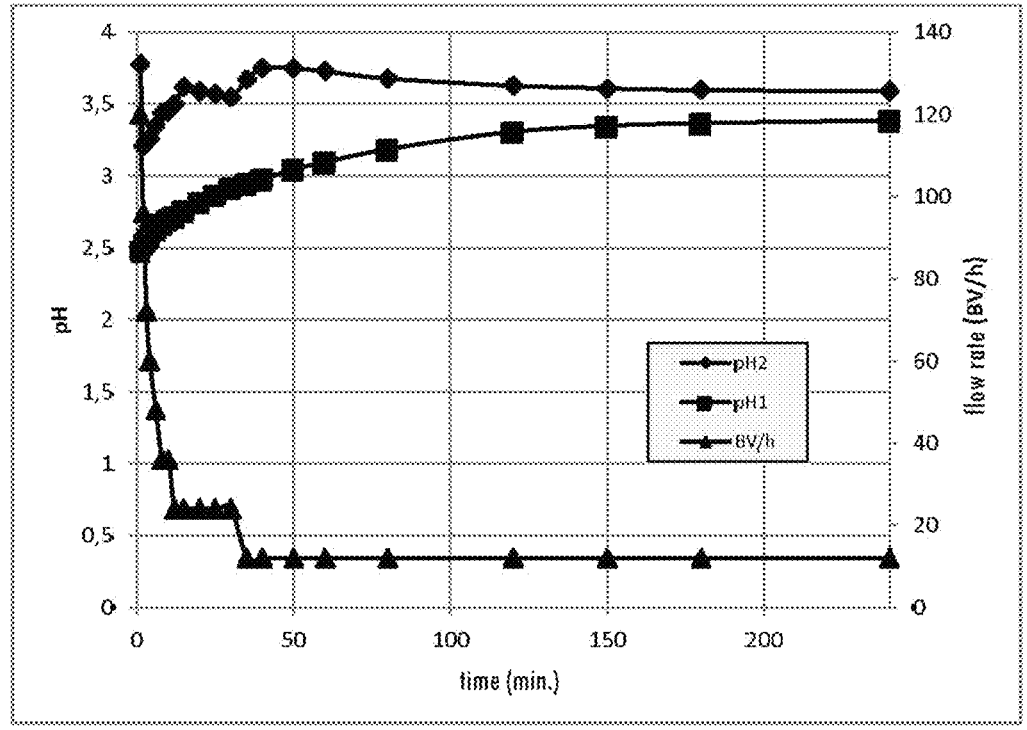
FIG. 6 is a graph showing the evolution of the pH values, and the circulation flow rate as a function of time for the deacidification experiments carried out with a first resin and with recirculation at a load of 10 BV.

FIG. 6 is a graph showing the evolution of pH1, pH2 and the flow rate expressed in BV/hour as a function of time for this $2^{nd}$ experiment with circulation in a loop of a cranberry juice load of 10 BV.

In light of table 12 and FIG. 6, one can in particular see that:
- the cranberry juice at the outlet of the column still had a pH below 4. The process according to the invention is therefore not able to alter the compounds of interest, such as anthocyans.
- after 240 minutes of experimentation, the pH of the cranberry juice in the container reached a substantially constant value of about 3.39, which is therefore very close to the set target value of 3.5;
- this $2^{nd}$ experiment thus corresponds to an implementation of the deacidification process according to the invention.

The $3^{rd}$ experiment was done with a cranberry juice load of 9 BV.

For this $3^{rd}$ experiment, table 13 below outlines, as a function of time (expressed in minutes):
- the pH1 and pH2 values;
- the flow rate of cranberry juice circulating in the column (expressed in mL/minutes and in BV/hour). The flow rate is always comprised between 10 BV/hour and 250 BV/hour.

TABLE 13 outlining the values of pH2, pH1 and the circulation flow rate of cranberry juice with a load of 9 BV

| Time (minutes) | pH2 | pH1 | Flow rate (mL/minute) | Flow rate (BV/hour) |
|---|---|---|---|---|
| 1 | 4.09 | 2.50 | 100 | 120 |
| 1.5 | 3.33 | 2.52 | 70 | 84 |
| 3 | 3.37 | 2.58 | 50 | 60 |
| 5 | 3.41 | 2.64 | 40 | 48 |
| 7 | 3.48 | 2.69 | 30 | 36 |
| 10 | 3.49 | 2.76 | 30 | 36 |
| 15 | 3.68 | 2.83 | 30 | 36 |
| 20 | 3.65 | 2.91 | 20 | 24 |
| 30 | 3.63 | 3.04 | 20 | 24 |
| 50 | 3.66 | 3.24 | 20 | 24 |
| 70 | 3.68 | 3.44 | 20 | 24 |
| 90 | 3.71 | 3.44 | 20 | 24 |
| 110 | 3.71 | 3.50 | 30 | 36 |

Figure 7:
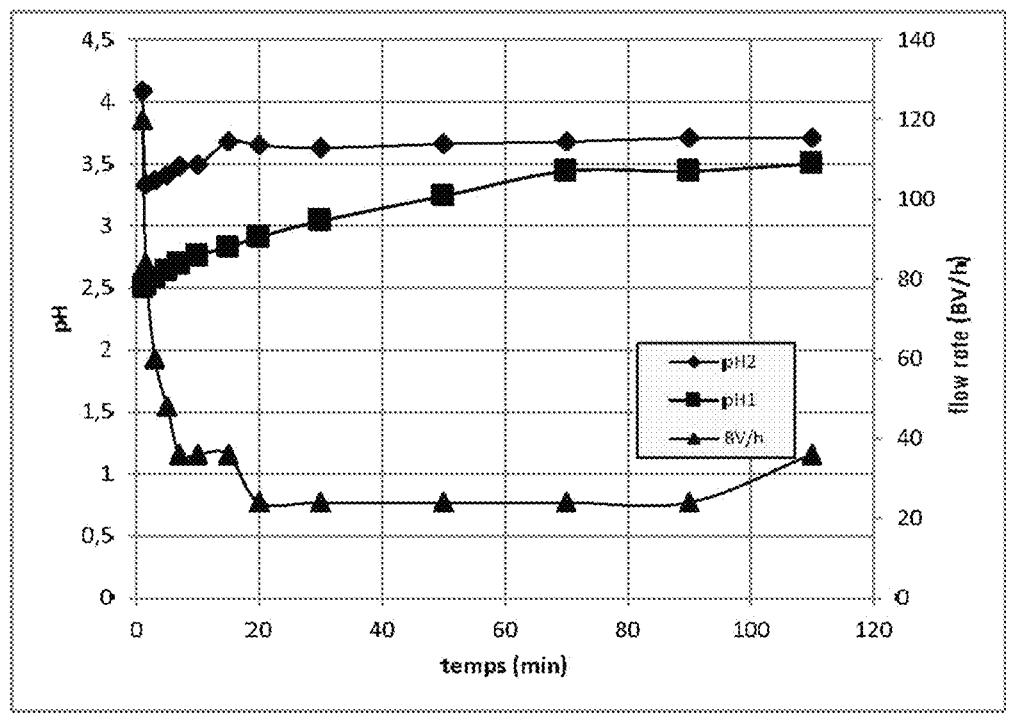
FIG. 7 is a graph showing the evolution of the pH values and the circulation flow rate as a function of time for deacidification experiments carried out with the first resin and with a circulation at a load of 9 BV.

FIG. 7 is a graph showing the evolution of pH1, pH2 and the flow rate expressed in BV/hour as a function of time for this 3$^{rd}$ experiment with circulation in a loop of a cranberry juice load of 9 BV.

In light of table 13 and FIG. 7, one can in particular see that:
- the cranberry juice at the outlet of the column still had a pH below 4. The process according to the invention therefore did not alter the compounds of interest, such as anthocyans.
- after 110 minutes of experimentation, the pH of the cranberry juice in the container reached the target value of 3.5;
- this 3$^{rd}$ experiment thus corresponds to an implementation of the deacidification process according to the invention.

The 4$^{th}$ experiment was done with a cranberry juice load of 9 BV.

For this 4$^{th}$ experiment, table 14 below outlines, as a function of time (expressed in minutes):
- the pH1 and pH2 values;
- the flow rate of cranberry juice circulating in the column (expressed in mL/minutes and in BV/hour). The flow rate is always comprised between 10 BV/hour and 250 BV/hour.

TABLE 14 outlining the values of pH2, pH1 and the circulation flow rate of cranberry juice with a load of 9 BV

| Time (minutes) | pH2 | pH1 | Flow rate (mL/minute) | Flow rate (BV/hour) |
|---|---|---|---|---|
| 1 | 4.66 | 2.49 | 310 | 40.4 |
| 3 | 3.62 | 2.57 | 310 | 40.4 |
| 4 | 3.66 | 2.58 | 310 | 40.4 |
| 7 | 3.63 | 2.64 | 200 | 26.1 |
| 9 | 3.8 | 2.67 | 130 | 17.0 |
| 11 | 4.06 | 2.7 | 130 | 17.0 |
| 13 | 4.12 | 2.73 | 130 | 17.0 |
| 15 | 4.1 | 2.76 | 130 | 17.0 |
| 17 | 4.01 | 2.78 | 130 | 17.0 |
| 19 | 3.96 | 2.81 | 130 | 17.0 |
| 25 | 3.8 | 2.88 | 130 | 17.0 |
| 28 | 3.87 | 2.92 | 100 | 13.0 |
| 31 | 3.83 | 2.95 | 100 | 13.0 |
| 34 | 3.94 | 2.97 | 100 | 13.0 |
| 45 | 3.85 | 3.06 | 100 | 13.0 |
| 55 | 3.78 | 3.12 | 100 | 13.0 |
| 70 | 3.67 | 3.21 | 100 | 13.0 |
| 85 | 3.6 | 3.27 | 100 | 13.0 |
| 100 | 3.54 | 3.32 | 100 | 13.0 |
| 120 | 3.5 | 3.35 | 100 | 13.0 |

Figure 8:
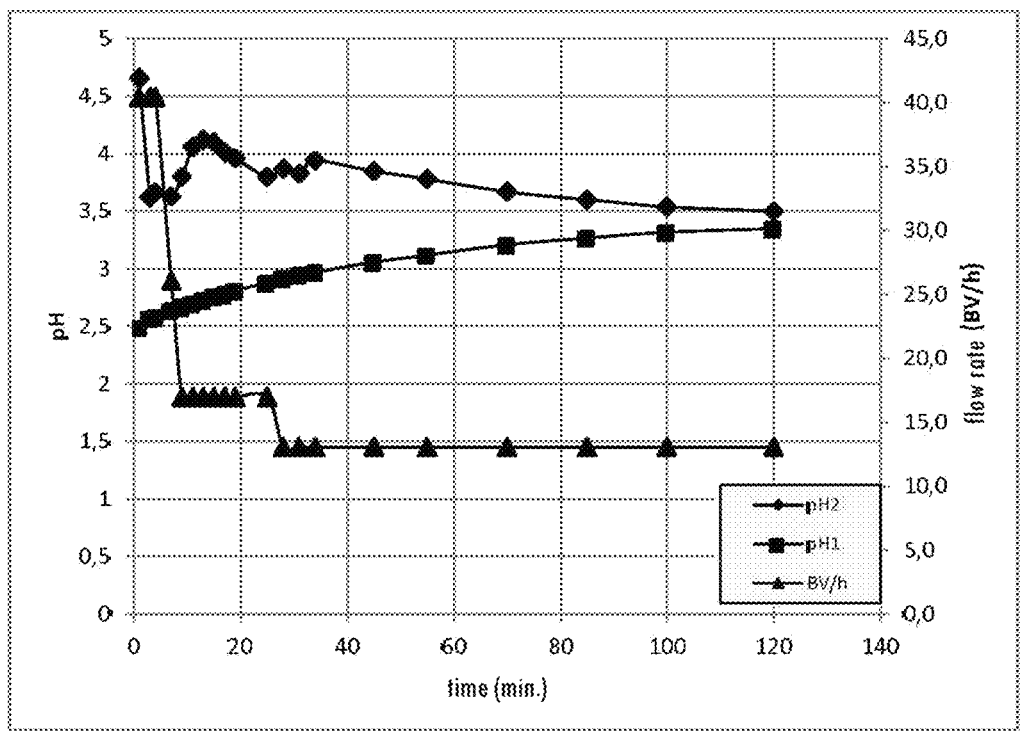
FIG. 8 is a graph showing the evolution of the pH values and the circulation flow rate as a function of time for deacidification experiments carried out with a first resin and with a recirculation a load of 9 BV.

FIG. 8 is a graph showing the evolution of pH1, pH2 and the flow rate expressed in BV/hour as a function of time for this 4$^{th}$ experiment with circulation in a loop of a cranberry juice load of 9 BV.

In light of table 14 and FIG. 8, one can in particular see that:
- the cranberry juice at the outlet of the column still had a pH below 5. The process according to the invention is therefore not likely to alter the compounds of interest, such as anthocyans.
- after 120 minutes of experimentation, the pH of the cranberry juice in the container reached a substantially constant value of about 3.35, which is therefore very close to the set target value of 3.5;
- this 4$^{th}$ experiment thus corresponds to an implementation of the deacidification process according to the invention.

The 5$^{th}$ experiment was done with a cranberry juice load of 8 BV. For this 5$^{th}$ experiment, table 15 below outlines, as a function of time (expressed in minutes): the pH1 and pH2 values and the flow rate of cranberry juice circulating in the column (expressed in mL/minutes and in BV/hour).

In this 5$^{th}$ experiment, during the first two minutes, the circulation flow rate of the cranberry juice in the column was 2.6 BV/hour, therefore less than 10 BV/hour.

Thus, during the first two minutes of this 5$^{th}$ experiment, the deacidification process according to the invention was not implemented. Below, we outline the consequences that this had on the cranberry juice to be de acidified.

TABLE 15 outlining the values of pH2, pH1 and the circulation flow rate of cranberry juice with a load of 8 BV

| Time (minutes) | pH2 | pH1 | Flow rate (mL/minute) | Flow rate (BV/hour) |
|---|---|---|---|---|
| 1 | 8.66 | 2.52 | 20 | 2.6 |
| 2 | 8.92 | 2.54 | 20 | 2.6 |
| 3 | 3.28 | 2.65 | 400 | 52.2 |
| 4 | 3.33 | 2.68 | 300 | 39.1 |
| 6 | 3.39 | 2.72 | 200 | 26.1 |
| 10 | 3.56 | 2.81 | 200 | 26.1 |
| 14 | 3.55 | 2.90 | 200 | 26.1 |
| 16 | 3.54 | 2.99 | 200 | 26.1 |
| 18 | 3.55 | 3.03 | 200 | 26.1 |
| 20 | 3.55 | 2.90 | 200 | 26.1 |
| 24 | 3.56 | 3.10 | 200 | 26.1 |
| 28 | 3.53 | 3.18 | 230 | 30.0 |
| 30 | 3.54 | 3.22 | 230 | 30.0 |
| 34 | 3.54 | 3.28 | 260 | 33.9 |
| 37 | 3.56 | 3.33 | 260 | 33.9 |
| 40 | 3.57 | 3.38 | 300 | 39.1 |
| 44 | 3.58 | 3.44 | 350 | 45.7 |
| 45 | 3.59 | 3.45 | 350 | 45.7 |
| 49 | 3.6 | 3.50 | 400 | 52.2 |

Figure 9:
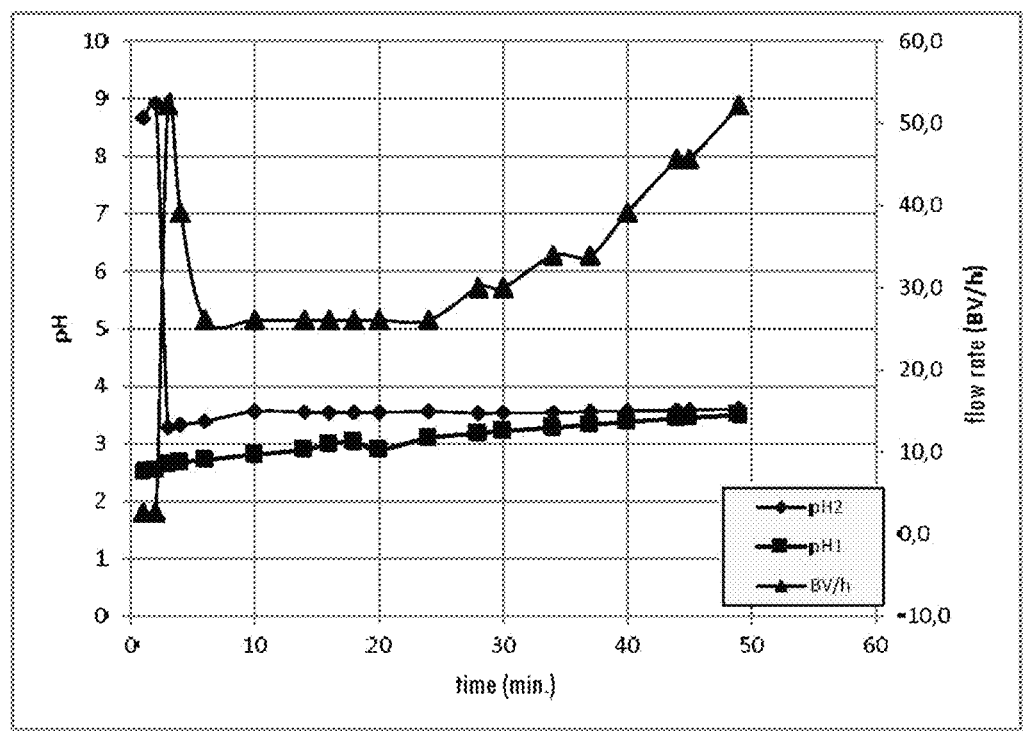
FIG. 9 is a graph showing the evolution of the pH values and the circulation flow rate as a function of time for deacidification experiments carried out with a first resin and with a recirculation at a load of 8 BV.

FIG. 9 is a graph showing the evolution of pH1, pH2 and the flow rate expressed in BV/hour as a function of time for this 5$^{th}$ experiment with circulation in a loop of a cranberry juice load of 9 BV.

In light of table 15 and FIG. 9, one can in particular see that:
- the fact that for the first two minutes of the experiment (i.e., of the circulation in a loop of the cranberry juice), the flow rate was only 2.6 BV/hour, had an impact on the pH value of the cranberry juice leaving the column at the beginning of the experiment, which was more than 8.5 (i.e., the pH value at which the compounds of interest such as the anthocyans are highly likely to be altered);
- once the flow rate increased, going from 2.6 BV/hour to 52.2 BV/hour, the pH of the cranberry juice immediately went from 8.92 to 3.28, i.e., the cranberry juice reached a pH value at which the compounds of interest are not altered;
- after 49 minutes of experimentation, the pH of the cranberry juice in the container reached the target value of 3.5.

This $5^{th}$ experiment thus attests to the significance of the fact that the circulation flow rate of the cranberry juice must be at least 10 BV/hour, as well as the significance of its regulation, and particularly at the beginning of the experiment, where it must be high in order for the cranberry juice not to have, upon leaving the column, a pH greater than the values at which the compounds of interest such as the anthocyans are likely to be altered.

With a column filled with resin 2, three experiments were done so as to vary the cranberry juice load to be deacidified (i.e., placed in circulation in a loop).

The $1^{st}$ experiment was done with a load of 6 BV.

For this $1^{st}$ experiment, table 16 below outlines, as a function of time (expressed in minutes):
- the pH1 and pH2 values;
- the flow rate of cranberry juice circulating in the column (expressed in mL/minutes and in BV/hour). The flow rate is always comprised between 10 BV/hour and 250 BV/hour.

TABLE 16 outlining the values of pH2, pH1 and the circulation flow rate of cranberry juice with a load of 6 BV

| Time (minutes) | pH2 | pH1 | Flow rate (mL/minute) | Flow rate (BV/hour) |
|---|---|---|---|---|
| 1 | 9.58 | 2.50 | 100 | 120 |
| 2 | 4.84 | 2.62 | 80 | 96 |
| 3 | 4.15 | 2.72 | 80 | 96 |
| 4 | 4.21 | 2.81 | 60 | 72 |
| 5 | 4.24 | 2.89 | 60 | 72 |
| 6 | 4.16 | 2.97 | 60 | 72 |
| 7 | 4.11 | 3.04 | 60 | 72 |
| 8 | 4.07 | 3.13 | 60 | 72 |
| 10 | 3.99 | 3.26 | 60 | 72 |
| 12 | 3.91 | 3.37 | 60 | 72 |
| 14 | 3.85 | 3.44 | 60 | 72 |
| 16 | 3.82 | 3.49 | 60 | 72 |
| 17 | 3.8 | 3.51 | 60 | 72 |
| 18 | 3.79 | 3.52 | 60 | 72 |

Figure 10:
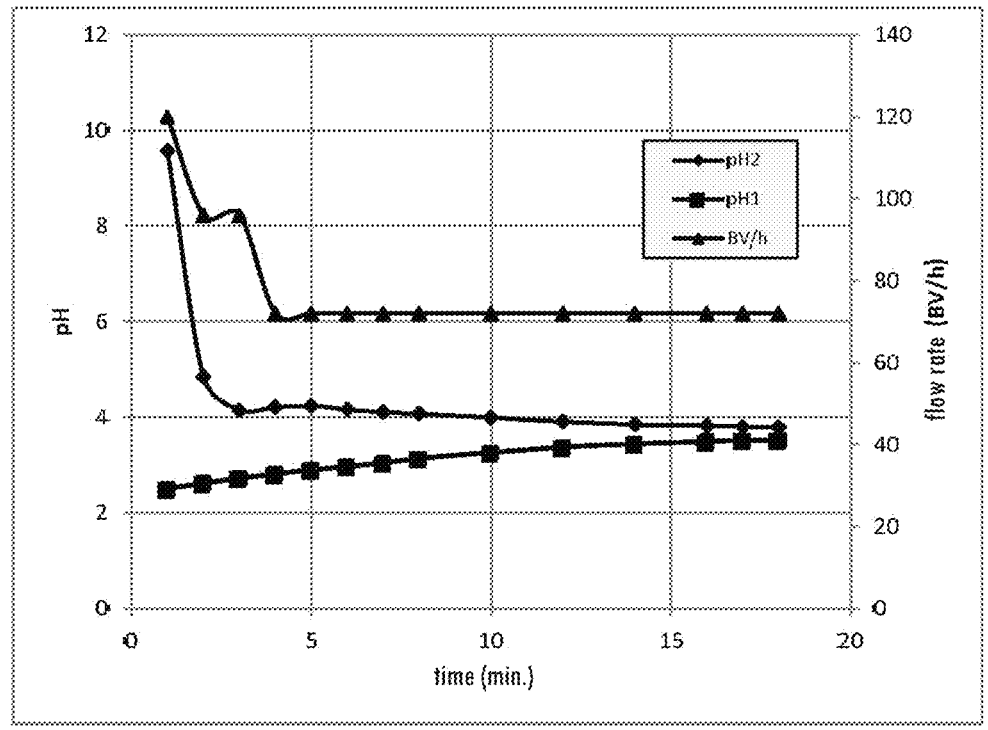
FIG. 10 is a graph showing the evolution of the pH values and the circulation flow rate as a function of time for deacidification experience carried out with a second resin and with a recirculation a load of 6 BV.

FIG. 10 is a graph showing the evolution of pH1, pH2 and the flow rate expressed in BV/hour as a function of time for this $1^{st}$ experiment with circulation in a loop with a cranberry juice load of 6 BV.

In light of table 16 and FIG. 10, one can in particular see that:
- despite a high circulation flow rate of 120 BV/hour at the beginning of the experiment, the pH value of the cranberry juice leaving the column was 9.58 (i.e., a pH value at which the compounds of interest such as the anthocyans are highly likely to be altered);
- next, after 2 minutes of experimentation, the pH values of the cranberry juice were still below 5 (i.e., pH values at which the compounds of interest are not likely to be altered);
- thus, the $1^{st}$ minute of experimentation, despite a very high circulation flow rate, could have been detrimental to the compounds of interest;
- with a load of 6 BV of cranberry juice and resin 2, a circulation flow rate higher than 120 BV/hour and/or another dimensioning of the column should be implemented to prevent, at the beginning of the experiment, compounds of interest from being altered due to the fact that the pH of the cranberry juice leaving the column is greater than 9;
- after 17 minutes of experimentation, the pH of the cranberry juice in the container has reached the target value of 3.5.

The $2^{nd}$ experiment was done with a load of 8 BV.

For this $2^{nd}$ experiment, table 17 below outlines, as a function of time (expressed in minutes):
- the pH1 and pH2 values;
- the flow rate of cranberry juice circulating in the column (expressed in mL/minutes and in BV/hour). The flow rate is always comprised between 10 BV/hour and 250 BV/hour.

TABLE 17 outlining the values of pH2, pH1 and the circulation flow rate of cranberry juice with a load of 8 BV

| Time (minutes) | pH2 | pH1 | Flow rate (mL/minute) | Flow rate (BV/hour) |
|---|---|---|---|---|
| 1 | 6.83 | 2.47 | 100 | 120 |
| 1.5 | 4.18 | 2.50 | 100 | 120 |
| 2 | 3.77 | 2.54 | 100 | 120 |
| 2.5 | 3.68 | 2.59 | 80 | 96 |
| 3 | 3.66 | 2.62 | 80 | 96 |
| 4 | 3.59 | 2.70 | 40 | 48 |
| 5 | 3.62 | 2.75 | 40 | 48 |
| 6 | 3.63 | 2.80 | 30 | 36 |
| 7 | 3.6 | 2.85 | 20 | 24 |
| 8 | 3.59 | 2.90 | 10 | 12 |

Figure 11:
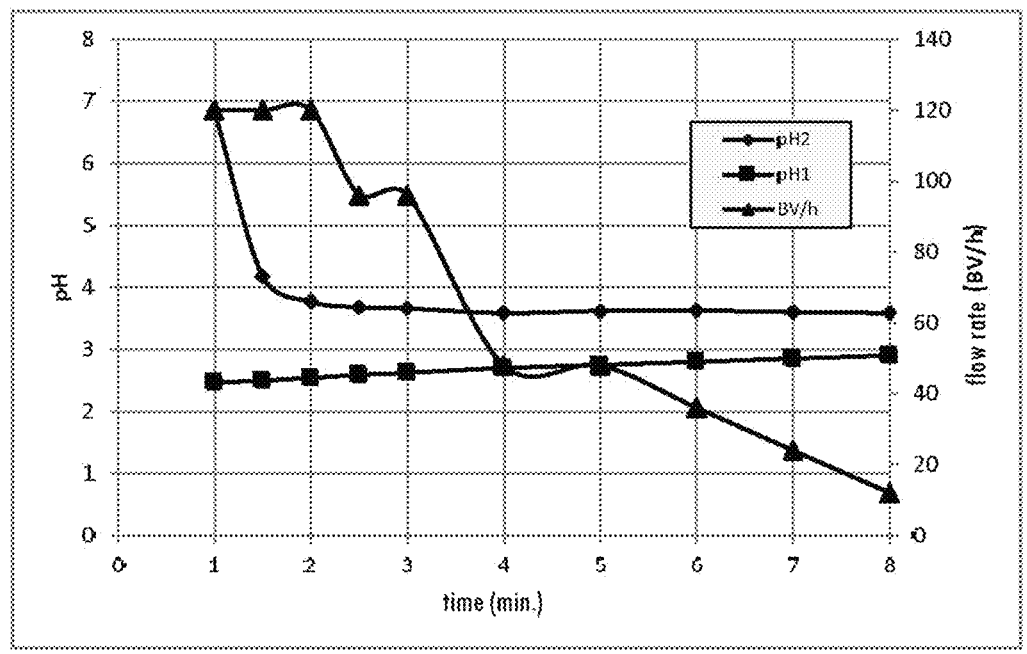
FIG. 11 is a graph showing the evolution of the pH values, and of the circulation flow rate, as a function of time for deacidification experiments carried out with a second resin and with a recirculation at a load of 8 BV.

FIG. 11 is a graph showing the evolution of pH1, pH2 and the flow rate expressed in BV/hour as a function of time for this $2^{nd}$ experiment with circulation in a loop with a cranberry juice load of 8 BV.

In light of table 17 and FIG. 11, one can in particular see that:
- despite a high circulation flow rate of 120 BV/hour at the beginning of the experiment, the pH value of the cranberry juice leaving the column was 6.83 (i.e., a moderately acceptable pH value, since compounds of interest such as the anthocyans may be altered);
- next, after 1.5 minutes of experimentation, the pH values of the cranberry juice were still below 4.55 (i.e., pH values at which the compounds of interest are not likely to be altered);
- the target value of 3.5 is not reached during this $2^{nd}$ experiment;
- thus, during this $2^{nd}$ experiment, aside from the fact that compounds of interest may have been altered, the circulation flow rate of the cranberry juice was not adjusted, such that the pH of the cranberry juice increases up to the target value of 3.5 that had been set.

The 3rd experiment was done with a load of 10 BV.

For this 3$^{rd}$ experiment, table 18 below outlines, as a function of time (expressed in minutes):
- the pH1 and pH2 values;
- the flow rate of cranberry juice circulating in the column (expressed in mL/minutes and in BV/hour). The flow rate is always comprised between 10 BV/hour and 250 BV/hour.

TABLE 18 outlining the values of pH2, pH1 and the circulation flow rate of cranberry juice with a load of 10 BV

| Time (minutes) | pH2 | pH1 | Flow rate (mL/minute) | Flow rate (BV/hour) |
|---|---|---|---|---|
| 1.5 | 2.96 | 2.54 | 100 | 120 |
| 2 | 4.41 | 2.51 | 100 | 120 |
| 3 | 3.61 | 2.59 | 80 | 96 |
| 4 | 3.53 | 2.59 | 60 | 72 |
| 5 | 3.52 | 2.71 | 60 | 72 |
| 8 | 3.51 | 2.81 | 40 | 48 |
| 9 | 3.48 | 2.88 | 40 | 48 |
| 11 | 3.45 | 2.92 | 30 | 36 |
| 13 | 3.43 | 2.94 | 20 | 24 |
| 16 | 3.45 | 2.97 | 10 | 12 |

Figure 12:
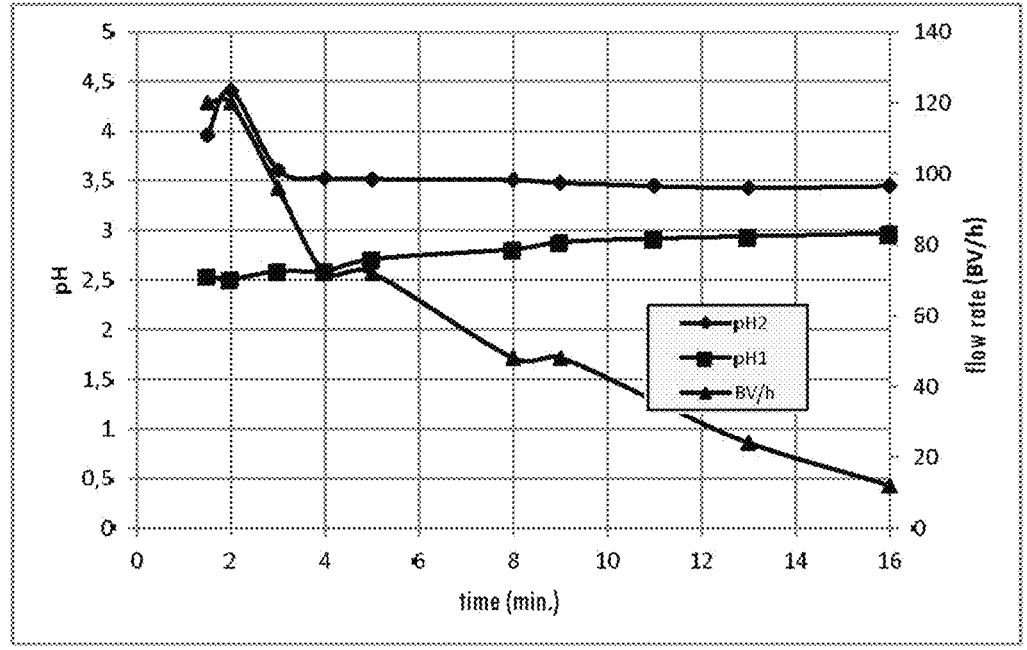
FIG. 12 is a graph showing the evolution of the pH values, and of the circulation flow rate as a function of time for deacidification experiments carried out with a second resin and with a recirculation at a load of 10 BV.

FIG. 12 is a graph showing the evolution of pH1, pH2 and the flow rate expressed in BV/hour as a function of time for this 3$^{rd}$ experiment with circulation in a loop with a cranberry juice load of 10 BV.

In light of table 18 and FIG. 12, one can in particular see that:
- the cranberry juice still had, upon leaving the column, a pH below 4.5. The process according to the invention is therefore not likely to alter the compounds of interest, such as the anthocyans;
- the target value of 3.5 was not reached during this 3$^{rd}$ experiment;
- with this 3$^{rd}$ experiment, the circulation flow rate of the cranberry juice was not adjusted, such that the pH of the cranberry juice increases up to the target value of 3.5 that had been set.

Table 19 is a summary table that outlines, according to the experiments done (i.e., experiments E1 to E5 with resin 1 and experiments E'1 to E'3 with resin 2):
- the volume of cranberry juice circulated in a bowl to be deacidified, in other words, the cranberry juice load to be deacidified. This volume is expressed in Bv;
- the concentration index expressed in degrees Brix (°Bx);
- the final pH at the end of the experiment;
- the duration of the experiment;
- the optical density of 420 nm, 520 nm, 620 nm and 280 nm;
- the intensity and shade;
- the relative optical density at 420 nm, 520 nm, 620 nm and 280 nm;
- the relative intensity and the relative shade;
- the malic acid and quinic acid concentrations in the deacidified cranberry juice;
- the ratio of these malic acid and quinic acid concentrations.

Furthermore, in a column titled "Raw juice", the characteristics of the raw cranberry juice are recalled, i.e., before deacidification thereof.

The optical density was measured by UV-visible spectrophotometry.

The intensity parameter corresponds to the sum of the values of the optical density at 420 nm, 520 nm and 620 nm.

The shade parameter corresponds to the ratio of the optical density at 420 nm to that at 520 nm.

The optical density at 280 nm provides an indication of the concentration of the carbon and double bond rings, which is therefore proportional to the concentration of the functional molecules.

The relative optical densities correspond to the optical densities divided by the concentration index expressed in degrees Brix of the corresponding cranberry juice. These relative optical density values account for the dilution effect due to the presence of water in the column. The same is true for the relative intensity and relative shade values.

The malic and quinic acid concentrations were determined by HPLC with the equipment described above.

During all of these experiments implementing the process according to the invention with resins 1 and 2, it should be noted that with a regulation of the circulation flow rate, the cranberry juice was able to be deacidified by going from a pH value of 2.47 to values close to the target value of 3.5. The initial circulation flow rate must therefore be very high so that the pH of the cranberry juice leaving the column is not too high (and therefore harmful for the compounds of interest) at the beginning of the experiment. Next, the circulation flow rate is gradually reduced, then stabilized around 20 BV/hour for resin 1 and 70 BV/hour for resin 2. Resin 2 has faster kinetics than resin 1, which requires regulating the pH of the cranberry juice well at the outlet of the column, and particularly at the beginning of the experiment.

TABLE 19 summarizing the results of the 8 experiments implementing the deacidification process according to the invention

| | Raw juice | Resin 1 | | | | | Resin 2 | | |
|---|---|---|---|---|---|---|---|---|---|
| | | E1 | E2 | E3 | E4 | E5 | E'1 | E'2 | E'3 |
| Volume of the resin (mL) | | 50 | 50 | 50 | 460 | 460 | 50 | 50 | 50 |
| V produced | | 8 | 10 | 9 | 9 | 8 | 6 | 8 | 10 |
| Brix (°B) | 7.6 | 5.4 | 5.4 | 5.3 | 5.4 | 7.4 | 5.0 | 5.6 | 5.9 |
| pH | 2.47 | 3.50 | 3.39 | 3.50 | 3.35 | 3.50 | 3.52 | 2.90 | 2.97 |
| Time (minutes) | | 47 | 240 | 110 | 120 | 49 | 18 | 8 | 16 |
| malic acid (g/L) | 9.47 | 5.35 | 6.35 | 5.26 | 4.88 | 6.32 | 4.59 | 5.40 | 6.35 |
| quinic acid (g/L) | 6.63 | 5.05 | 5.55 | 4.92 | 4.85 | 6.01 | 4.00 | 4.73 | 5.55 |
| quinic acid/malic acid ratio | 0.70 | 0.94 | 0.87 | 0.94 | 0.99 | 0.95 | 0.87 | 0.88 | 0.87 |

TABLE 19-continued summarizing the results of the 8 experiments
implementing the deacidification process according to the invention

|  | Raw juice | Resin 1 | | | | | Resin 2 | | |
|---|---|---|---|---|---|---|---|---|---|
|  |  | E1 | E2 | E3 | E4 | E5 | E'1 | E'2 | E'3 |
| Optical density: |  |  |  |  |  |  |  |  |  |
| 420 nm | 1.625 | 1.240 | 1.240 | 1.030 | 1.390 | 1.830 | 0.560 | 0.925 | 1.130 |
| 520 nm | 2.705 | 2.16 | 2.390 | 1.910 | 2.545 | 2.770 | 1.115 | 2.085 | 2.675 |
| 620 nm | 0.230 | 0.175 | 0.160 | 0.150 | 0.220 | 0.279 | 0.065 | 0.065 | 0.090 |
| 280 nm | 29.320 | — | — | — | — | 25.020 | — | — | — |
| intensity | 4.560 | 3.580 | 3.790 | 3.090 | 4.160 | 4.880 | 1.740 | 3.080 | 3.900 |
| shade | 0.600 | 0.570 | 0.520 | 0.540 | 0.550 | 0.660 | 0.500 | 0.440 | 0.420 |
| Relative optical density: |  |  |  |  |  |  |  |  |  |
| 420 nm | 0.21 | 0.23 | 0.23 | 0.19 | 0.26 | 0.25 | 0.11 | 0.17 | 0.19 |
| 520 nm | 0.36 | 0.40 | 0.44 | 0.36 | 0.47 | 0.37 | 0.22 | 0.37 | 0.45 |
| 620 nm | 0.03 | 0.03 | 0.03 | 0.03 | 0.04 | 0.04 | 0.01 | 0.01 | 0.02 |
| 280 nm | 3.86 | — | — | — | — | 3.38 | — | — | — |
| relative intensity | 0.60 | 0.66 | 0.70 | 0.58 | 0.77 | 0.66 | 0.29 | 0.14 | 0.11 |
| relative shade | 0.08 | 0.11 | 0.10 | 0.10 | 0.10 | 0.09 | 0.10 | 0.08 | 0.07 |

In light of table 19, we note that:
resin 1 has an exchange capacity 50 times greater than resin 2. Indeed, with resin 1, it is possible to deacidify up to about 9 BV of the cranberry juice while keeping the pH at 3.5, whereas it is necessary to limit the load to 6 BV with resin 2 to guarantee the level of 3.5 pH units;
under these conditions, resin 2 causes a significant decrease in the colored intensity: the raw juice being at 0.60 and reaches 0.77 at pH 3.5 with resin 1 but only 0.29 with resin 2;
the process according to the invention increases the ratio of the concentration of quinic acid to that of malic acid: it goes from 0.7 to 0.9-1 in the deacidified juice;
the malic acid decreases in concentration significantly more than the quinic acid.

According to the inventive process, the juices obtained from 10 tests were mixed and concentrated at 50 Brix. The concentrated deacidified juice is compared to the raw concentrated juice. We note:
a decrease of 20% of the malic acid
a constant concentration in quinic acid
the quantity of cations (such as sodium, potassium, magnesium and calcium) has not varied during the process.

The total proanthocyanidins of the deacidified juice according to the inventive process were assayed using the *Multi-laboratory validation of standard method for quantifying proanthocyanidins in cranberry powders* process, Wiley Interscience, 2010, and the results are shown in the following table in A2 dimer proanthocyanidin equivalent.

| Sample | Total Proanthocyanidins (Eq. A2 Dimer) mg/L |
|---|---|
| Cranberry juice to be deacidified | 159.2 |
| Deacidified cranberry juice | 159.8 |

The scanning of the components (identified in the table below) was done using a liquid chromatography and quad time-of-flight (UPLC-QTOF) system in negative mode. The samples were filtered. After computer processing, the exact masses obtained were grouped together by families after identification using the databank. The following table shows the sum of the areas obtained for all of the families.

|  | Untreated cranberry juice | | Treated cranberry juice | |
|---|---|---|---|---|
| Families | Area | % (total) | Area | % (total) |
| Proanthocyanidins | 2941 | 8.8 | 4164 | 9.5 |
| Phenolic acids | 20315 | 61.0 | 26266 | 60.1 |
| Flavonoids | 10063 | 30.2 | 13277 | 30.4 |
| Total | 33319 | 100.0 | 43708 | 100.0 |

Scanning of the Components

| Phenolic acids | Proanthocyanidins | Flavonoids |
|---|---|---|
| 2-hydroxybenzoic acid | (−)-Epicatechin | 3-Hydroxyphloretin 2'-O-glucoside |
| 3-hydroxybenzoic acid | (−)-Epigallocatechin | Apigenin |
| 3-Methyl catechol | (+)-Catechin | Apigenin 6-C-glucoside |
| 4,6,3',4'-Tetramethoxyaurone | (+)-Catechin 3-O-gallate | Apigenin 7-O-glucoronide |
| 4-Hydroxybenzaldehyde | (+)-Catechin 3-O-glucose | Dihydromyricetin 3-O-rhamnoside |
| 4-hydroxybenzoic acid | PAC A2 | Dihydroquercetin |
| 4-Hydroxycoumarin | PAC B2 | Fisatin |
| 4-hydroxyphenyl acetic acid | A trimers | Isorhamnetin |
| r-Vinylguaiacol | B trimers | Isorhamnetin 3-O-glucoronide |
| r-Vinylphenol |  | Kaempferol-glucoside/galactoside |

-continued

| Phenolic acids | Proanthocyanidins | Flavonoids |
|---|---|---|
| 5,5'-dehydrodiferulic acid | | Kaempferol-glucuronide |
| 5-O-galloylquinic acid | | Methyl quercetin |
| Benzoic acid | | Myricetin |
| Caffeic acid | | Myricetin 3-O-arabinoside |
| Caffeoyl glucose | | Myricetin glycoside/galactoside |
| Catechol | | Phloretin |
| Chlorogenic acid | | Quercetin |
| Cinnamic acid | | Quercetin 3-O-arabinoside |
| Cinnamoyl glucose | | Quercetin 3-O-glucoronide |
| Coumarin | | Quercetin 3-O-xyloside |
| Coumaroyl glucoside | | Quercetin-glucoside/galactoside |
| Dihydro-p-coumaric acid | | Resveratrol |
| Ellagic acid | | Resveratrol-3-O-glucoside |
| Ellagic acetyl-arabinoside acid | | Rutin |
| Ferroloyl glucoside | | |
| Gallic acid | | |
| 3-O-gallate gallic acid | | |
| Galloyl glucose | | |
| Hydroxycaffeic acid | | |
| M-coumaric acid | | |
| O-coumaric acid | | |
| p-Anisaldehyde | | |
| p-coumaric acid | | |
| p-Anisaldehyde | | |
| p-coumaric acid | | |
| Ethyl ester p-coumaric acid | | |
| p-HPEA-EA | | |
| Protocatechuic acid | | |
| Pterostilbene | | |
| Pyrethin II | | |
| Pyrogallol | | |
| Sinapaldehyde | | |
| Sinapinic acid | | |
| Syringic acid | | |
| Syrigin | | |
| Vanillic acid | | |

What clearly emerges from the characterization is that the content in compounds of interest such as proanthocyanidins, phenolic acids, flavonoids and certain important cations of the deacidified cranberry juice is substantially the same as the cranberry juice to be deacidified.

Figure 13:
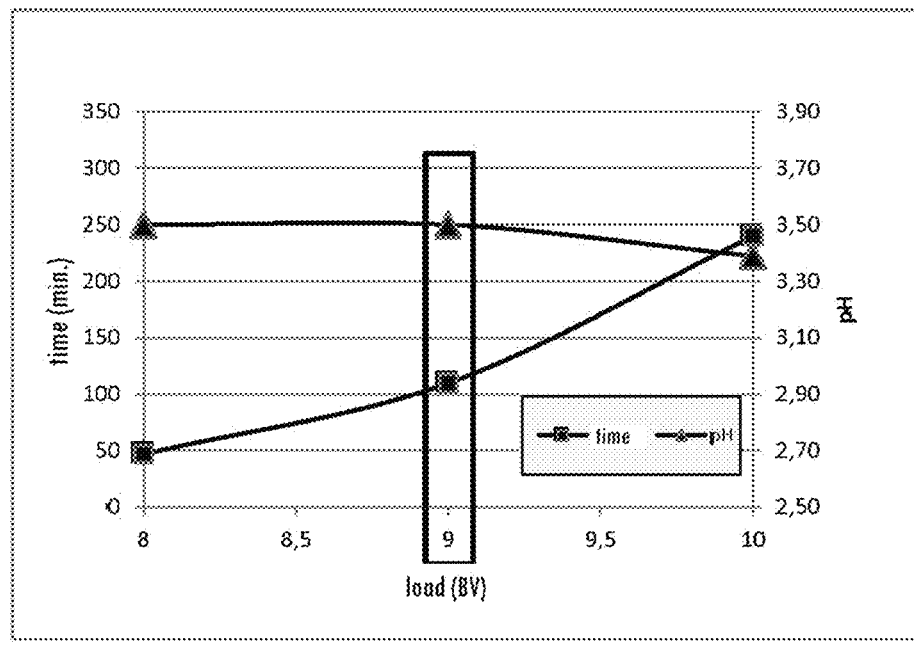
FIG. 13 is a graph showing the variation of the duration of the experiment, of the pH at the end of the experiment as a function of the cranberry juice load to be deacidified for the experiments done with the first resin.

FIG. 13 is a graph showing the variation of the duration of the experiment, the pH at the end of the experiment as a function of the cranberry juice load to be deacidified for the 5 experiments done with resin 1.

In light of the graph of FIG. 13, one can see that the optimal load of cranberry juice to be deacidified when the column is filled with resin 1 is 9 BV.

Figure 14:
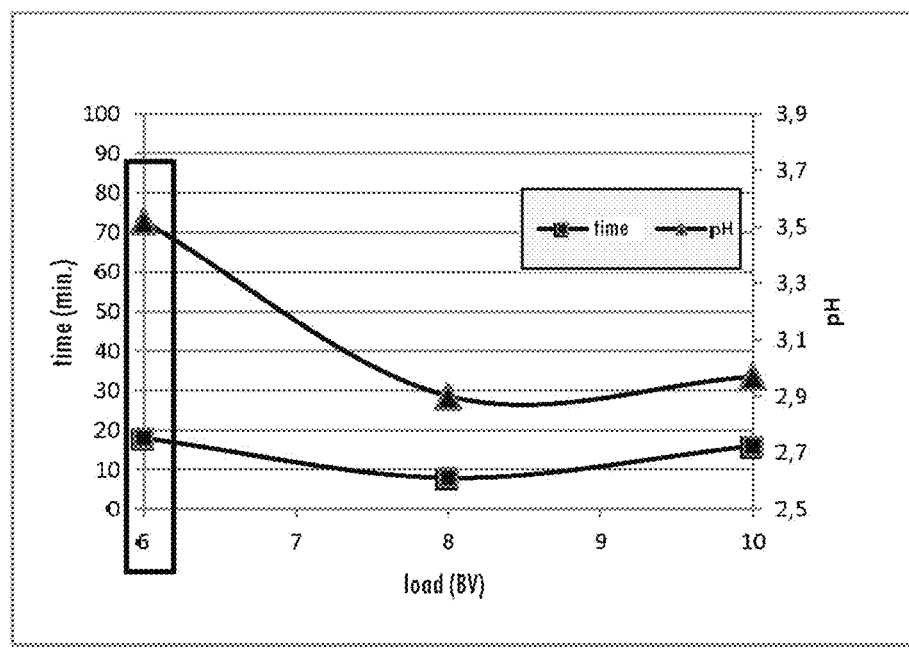
FIG. 14 is a graph showing the variation of the duration of the experiment, of the pH at the end of the experiment as a function of the cranberry juice load to be deacidified for experiments done with the second resin.

FIG. 14 is a graph showing the variation in the duration of the experiment, the pH at the end of the experiment as a function of the cranberry juice load to be deacidified for the 3 experiments done with resin 2.

In light of this graph of FIG. 14, one can see that the optimal load of cranberry juice to be deacidified when the column is filled with resin 2 is 6 BV.

For the $3^{rd}$ experiment with resin 1, the saturation of the resin was done with 2 BV of hydrochloric acid (1 mol/L-73 g/L of resin) at a flow rate of 2 BV/hour in an up flow mode, followed by slow rinsing with 2 BV of water at a flow rate of 2 BV/hour using an up flow mode.

During the saturation, the acids fixed by the resin are released by the passage of hydrochloric acid.

Table 20 below outlines the concentrations in chlorides and malic and quinic acid in the effluent recovered at the outlet for resin 1, and as a function of the BV of hydrochloric acid, then of water having circulated in resin 1 to respectively saturate and rinse it. The BV is expressed cumulatively. This thereby makes it possible to track the evolution of the chloride, malic and quinic acid concentrations as a function of the progression of the saturation of resin 1, then its rinsing.

TABLE 20 outlining the concentrations in chlorides and malic and quinic acids during the saturation with hydrochloric acid, then rinsing of resin 1

| phase | BV | Chloride concentration (g/L) | Malic acid concentration g/L | Quinic acid concentration g/L |
|---|---|---|---|---|
| Hydrochloric acid | 0.5 | 0.00 | 0.10 | 0.67 |
| | 1 | 0.00 | 0.10 | 0.63 |
| | 1.5 | 0.00 | 0.16 | 0.86 |
| | 2 | 0.00 | 8.56 | 2.95 |
| Water | 2.5 | 0.00 | 15.48 | 2.41 |
| | 3 | 1.10 | 16.49 | 2.22 |
| | 3.5 | 0.50 | 9.83 | 1.47 |
| | 4 | 0.30 | 4.77 | 0.78 |

Figure 15:
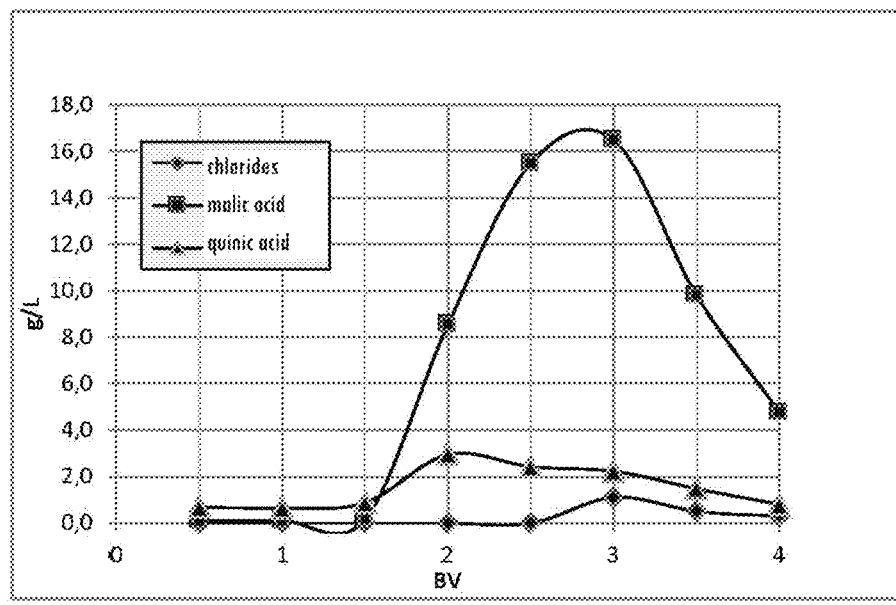
FIG. 15 is a graph of the evolution of the chloride, malic acid and quinic acid concentrations as a function of the cumulative BV of hydrochloric acid, then water.

FIG. 15 is a graph of the evolution of the chloride, malic acid and quinic acid concentrations as a function of the cumulative BV of hydrochloric acid, then water.

For the $1^{st}$ experiment with resin 2, the saturation of the resin was done with 2 BV of hydrochloric acid (1 mol/L; 73 g/L of resin) at a flow rate of 2 BV/hour in an up flow mode, followed by slow rinsing with 2 BV of water at a flow rate of 2 BV/hour using an up flow mode.

Table 21 below outlines the concentrations in chlorides and malic and quinic acids in the effluent recovered at the outlet for resin 2, as a function of the BV of hydrochloric acid, then of water having circulated in resin 2 to respectively saturate and rinse it. The BV is expressed cumulatively.

TABLE 21 outlining the concentrations in chlorides and malic and quinic acids during the saturation with hydrochloric acid, then rinsing of resin 2

| phase | BV | Chloride concentration (g/L) | Malic acid concentration g/L | Quinic acid concentration g/L |
|---|---|---|---|---|
| Hydrochloric acid | 0.5 | 0.00 | 0.17 | 0.27 |
|  | 1 | 0.00 | 0.15 | 0.22 |
|  | 1.5 | 0.00 | 0.14 | 0.20 |
|  | 2 | 0.00 | 0.90 | 0.17 |
| Water | 2.5 | 9.70 | 27.70 | 0.00 |
|  | 3 | 20.90 | 17.30 | 0.00 |
|  | 3.5 | 13.10 | 7.53 | 0.00 |
|  | 4 | 3.80 | 2.73 | 0.00 |

Figure 16:
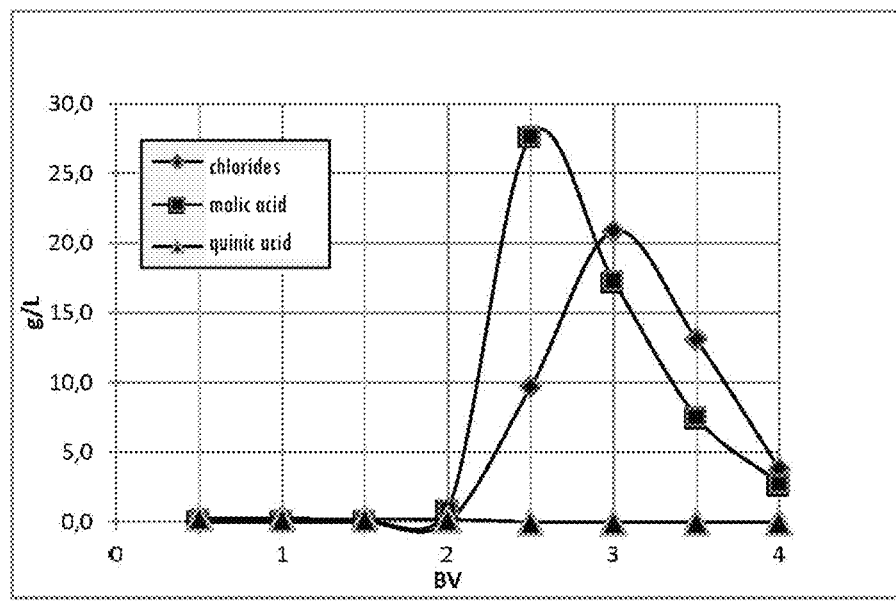
FIG. 16 is a graph of the evolution of the concentration in chlorides, malic acid and quinic acid as a function of the cumulative BV of hydrochloric acid, then water.

FIG. 16 is a graph of the evolution of the concentration in chlorides, malic acid and quinic acid as a function of the cumulative BV of hydrochloric acid, then water.

In light of tables 20 and 21 and FIGS. 15 and 16, one will note that:

resin 1 has a greater exchange capacity, since resin 2 has practically no excess chlorides in the recovered fraction, whereas on average, 10 g/L of residual chlorides is measured in the fraction recovered with resin 2. Approximately ⅓ of the chlorides is not used during the saturation with resin 2.

D—Example of Formulations for Grenadine Syrup

Table 22 below outlines:

the formulation of a grenadine syrup containing cranberry juice deacidified with the process according to the invention, i.e., a "formulation according to the invention";

the equivalent formulation of a grenadine syrup that is traditionally implemented, i.e., a "comparative formulation".

TABLE 22 outlining the formulations of grenadine syrup according to the invention and comparison

|  | Comparative formulation (kg) | Inventive formulation (kg) |
|---|---|---|
| Isoglucose syrup at 65/70° Bx | 3000 | 2700 |
| Cranberry juice at 55° Bx deacidified according to the invention | 0 | 300 |
| Grenadine flavoring | 20 | 20 |
| Water | 850 | 905 |
| Citric acid in solution | 55 | 0 |
| Dye E122 | 0.55 | 0 |
| Vanilla flavoring | 1 | 0 |
| Dye E124 | 0.55 | 0 |
| Total mass | 3927.1 | 3926 |

The citric acid was in solution in water at a concentration of 150 g/L.

The formulation of grenadine syrup according to the invention has the advantages relative to the comparative equivalent formulation of being free of any dyes, as well as citric acid, which is a food additive used as an acidity corrector, but also known to cause dental problems.

E—Example of Cranberry/Raspberry Syrup Formulations

Table 23 outlines below:

the formulation of a cranberry and raspberry syrup containing cranberry juice deacidified with the process according to the invention, i.e., a "formulation according to the invention";

the equivalent formulation of a cranberry/raspberry syrup that is traditionally implemented, i.e., a "comparative formulation".

TABLE 23 outlining the formulations of cranberry/raspberry syrup according to the invention and comparison

|  | Comparative formulation (kg) | Inventive formulation (kg) |
|---|---|---|
| Cranberry juice deacidified according to the invention | 0 | 513.3 |
| Cranberry juice not deacidified 65° Bx | 14 | 14 |
| Isoglucose syrup 65° Bx | 3000 | 2700 |
| Red grape juice 65° Bx | 15 | 0 |
| Citric acid in solution | 185 | 0 |
| Raspberry and cranberry flavoring | 8.6 | 8.6 |
| Dye E124 | 0.3 | 0 |
| Elderberry juice 65° Bx | 13 | 0 |
| Raspberry juice 65° Bx | 15 | 15 |
| Total mass | 3250.9 | 3250.9 |

The formulation of the cranberry and raspberry syrup according to the invention has the advantages, relative to the comparative equivalent formulation, of:

having no dye E124 and citric acid;

having replaced part of the sugar from the isoglucose syrup, as well as the sugar from the elderberry and grape syrups, with the deacidified cranberry juice according to the inventive process.

It should be noted that the comparative formulation comprises non-deacidified cranberry juice.

Having deacidified the cranberry juice with the process according to the invention makes it possible to have a formulation of cranberry and raspberry syrup that comprises more cranberry juice than the comparative equivalent formulation, and therefore to better leverage the cranberry juice.

The cranberry and raspberry syrup formulation is perceived as more natural. It further makes it possible to declare a higher red fruit content than the comparative formulation whose read for content consists of the content in non-deacidified cranberry juice plus that of the raspberry and cranberry flavoring.

F—Cranberry Sorbet Formulation

Table 24 below outlines a cranberry-based sorbet formulation deacidified using the process according to the invention.

TABLE 24 outlining a sorbet formulation based on cranberry juice
deacidified according to the invention

|  | Quantity (g) |
| --- | --- |
| Deacidified cranberry juice 7.6° Bx | 930 |
| Natural flavorings | 10 |
| Fructose syrup 70° Bx | 60 |
| Total | 1000 |

The low acidity of the cranberry juice deacidified using the process according to the invention makes it possible to produce a sorbet formulation containing this cranberry juice in a large quantity (weight content 93% relative to the total weight of the sorbet). The very small quantities of fructose syrup and natural flavorings (weight contents of 1% and 6%, respectively, relative to the total mass of the sorbet), as well as the absence of any dietary additive and dye in the sorbet formulation, attest to a very natural and "pure fruit" product.

G—Cooking Sauce Formulation of the Barbecue Sauce Type

In this savory product example, the fruity notes of the cranberry, without its drawbacks in terms of acidity and astringency, are associated with traditional notes of the barbecue type, namely smokiness, providing a sugar/salt balance to the sauce.

All of the ingredients of the sauce outlined in table 25 below were mixed and heat-treated at 85° C. for 5 minutes in order to preserve the freshness of the product, which was next pasteurized and aseptically packaged.

TABLE 25 outlining a cooking sauce formulation of the barbecue type
with a base of cranberry juice deacidified according to the invention.

|  | Quantity (g) |
| --- | --- |
| Deacidified cranberry juice 7.6° Brix | 550 |
| Deacidified cranberry juice 55° Brix | 255 |
| salt | 87 |
| Natural flavorings (fried onion and spices) | 12 |
| Smoke and meat flavorings (fried onion and spices) | 5 |
| Total | 1000 |

The invention claimed is:

1. A method for deacidifying a cranberry juice to be deacidified, comprising:
eluting the cranberry juice to be deacidified on a weak anion exchange resin to lead to a deacidified cranberry juice after elution;
wherein the weak anion exchange resin is a resin of the acrylic or styrene type; and
the eluting step further comprises eluting the cranberry juice to be deacidified on said resin at a rate equal to or greater than 10 bed volume hour (BV/h);
wherein the deacidified cranberry juice, comprises:
a pH of between 32 and 3.8
a quinic acid/malic acid ratio of from about 0.85 to about 0.99;
no added sugars;
no masking agents; and
no buffer.

2. The deacidified cranberry juice according to claim 1, wherein the total proanthocyanidin content of the deacidified cranberry juice does not vary outside the range of 95-105% of a cranberry juice to be deacidified having led to said deacidified cranberry juice.

3. The deacidified cranberry juice according to claim 1, wherein the content in inorganic cations of the deacidified cranberry juice does not vary outside the range of 95-105% of a cranberry juice to be deacidified having led to said deacidified cranberry juice.

4. The deacidified cranberry juice according to claim 1, wherein the content of two, three or four of proanthocyanidins, phenolic acids, flavonoids and organic cations of said deacidified cranberry juice is not substantially lower than the content of the cranberry juice to be deacidified.

5. The deacidified cranberry juice according to claim 1, wherein the organic cations are potassium, calcium and sodium.

6. A method for deacidifying a cranberry juice to be deacidified, comprising:
eluting the cranberry juice to be deacidified on a weak anion exchange resin to lead to a deacidified cranberry juice after elution;
wherein
the weak anion exchange resin is a resin of the acrylic or styrene type; and
the eluting step further comprises eluting the cranberry juice to be deacidified on said resin at a rate, in bed volume/hour (BV/h) wherein the deacidified cranberry juice has a pH that is greater than the first pKa of the first acidity of malic acid and smaller than the pKa of benzoic acid.

7. The method according to claim 6, wherein the anion exchange resin is an acrylic anion exchange resin.

8. The method according to claim 7, wherein the acrylic anion exchange resin has a capacity between 1.6-3.2 equivalent/L.

9. The method according to claim 7, wherein the acrylic anion exchange resin has an initial exchange speed equal to or greater than +0.10 unit of pH/minute observed after 5 minutes of contact of the cranberry juice to be deacidified with the acrylic anion exchange resin in a volume ratio of 5:1 of the cranberry juice to be deacidified to the acrylic anion exchange resin.

10. The method according to claim 6, further comprising a step consisting of clarifying the cranberry juice to be deacidified until obtaining a turbidity below 500 Nephelometric Turbidity Unit (NTU) before said step of eluting the cranberry juice to be deacidified.

11. The method according to claim 6, wherein the step of eluting is carried out in a column containing the weak anion exchange resin, and said step of eluting consists of circulating said cranberry juice to be deacidified on said weak anion exchange resin at least once.

12. The method according to claim 11, wherein the step of eluting consists of circulating a volume of said cranberry juice to be deacidified in about 1 to 20 bed volume (BV).

13. A food composition, wherein it comprises cranberry juice according to claim 1.

14. A method for preventing a urinary infection, comprising administering the food composition according to claim 13.

15. The method according to claim 6, wherein said cranberry juice to be deacidified has a pH from 2.3 to 2.5.

16. The method according to claim 6, wherein said deacidified cranberry juice has a quinic acid/malic acid ratio from 0.85 to 0.99.

17. The method according to claim 6, wherein said deacidified cranberry juice has a pH of between 3.2 and 3.8.

18. The method according to claim 6, wherein the pH of the deacidified cranberry juice does not exceed the pKa of benzoic acid at any time during the eluting step.

19. The method according to claim 6, wherein the pH of the deacidified cranberry juice does not exceed a pH of 6 at any time during the eluting step.

* * * * *